(12) United States Patent
Yu

(10) Patent No.: US 11,939,306 B2
(45) Date of Patent: *Mar. 26, 2024

(54) CRYSTAL FORMS OF IMMUNOMODULATORS

(71) Applicant: Curis, Inc., Lexington, MA (US)

(72) Inventor: Shu Yu, Suzhou (CN)

(73) Assignee: Curis, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,387

(22) Filed: Jan. 25, 2023

(65) Prior Publication Data

US 2023/0167077 A1   Jun. 1, 2023

Related U.S. Application Data

(63) Continuation of application No. 17/350,445, filed on Jun. 17, 2021, now Pat. No. 11,643,401, which is a continuation of application No. 16/651,830, filed as application No. PCT/US2018/053052 on Sep. 27, 2018, now Pat. No. 11,040,948.

(30) Foreign Application Priority Data

Sep. 29, 2017   (WO) ................ PCT/CN2017/104485

(51) Int. Cl.
C07D 271/06   (2006.01)

(52) U.S. Cl.
CPC ........ C07D 271/06 (2013.01); *C07B 2200/13* (2013.01)

(58) Field of Classification Search
CPC .................................................. C07D 271/06
See application file for complete search history.

(56) References Cited

U.S. PATENT DOCUMENTS

| | | | |
|---|---|---|---|
| 3,227,725 | A | 1/1966 | Fernand et al. |
| 5,387,585 | A | 2/1995 | Borer et al. |
| 5,665,718 | A | 9/1997 | Godel et al. |
| 8,735,553 | B1 | 5/2014 | Li et al. |
| 9,771,338 | B2 | 9/2017 | Sasikumar et al. |
| 10,173,989 | B2 | 1/2019 | Sasikumar et al. |
| 10,590,093 | B2 | 3/2020 | Sasikumar et al. |
| 10,781,189 | B2 | 9/2020 | Sasikumar et al. |
| 10,961,205 | B2 | 3/2021 | Sasikumar et al. |
| 11,040,948 | B2 | 6/2021 | Yu |
| 11,136,300 | B2 | 10/2021 | Sasikumar et al. |
| 11,465,976 | B2 | 10/2022 | Sasikumar et al. |
| 11,497,734 | B2 | 11/2022 | Sasikumar et al. |
| 11,497,735 | B2 | 11/2022 | Sasikumar et al. |
| 11,643,401 | B2 | 5/2023 | Yu |
| 11,680,051 | B2 | 6/2023 | Sasikumar et al. |
| 2005/0272779 | A1 | 12/2005 | Edwards et al. |
| 2007/0197522 | A1 | 8/2007 | Edwards et al. |
| 2007/0225332 | A1 | 9/2007 | Gu et al. |
| 2009/0099227 | A1 | 4/2009 | Fyfe et al. |
| 2011/0275673 | A1 | 11/2011 | Xiang et al. |
| 2013/0022629 | A1 | 1/2013 | Sharpe et al. |
| 2014/0199334 | A1 | 7/2014 | Sasikumar et al. |
| 2014/0235620 | A1 | 8/2014 | Caferro et al. |
| 2015/0073024 | A1 | 3/2015 | Sasikumar et al. |
| 2015/0073042 | A1 | 3/2015 | Sasikumar et al. |
| 2018/0044303 | A1 | 2/2018 | Sasikumar et al. |
| 2020/0061030 | A1 | 2/2020 | Sasikumar et al. |
| 2020/0239422 | A1 | 7/2020 | Sasikumar et al. |
| 2020/0247766 | A1 | 8/2020 | Yu |
| 2020/0289477 | A1 | 9/2020 | Sasikumar et al. |
| 2020/0368210 | A1 | 11/2020 | Sasikumar et al. |
| 2021/0380544 | A1 | 12/2021 | Yu |
| 2022/0048875 | A1 | 2/2022 | Sasikumar et al. |
| 2023/0062570 | A1 | 3/2023 | Sasikumar et al. |
| 2023/0081191 | A1 | 3/2023 | Govindan et al. |
| 2023/0110077 | A1 | 4/2023 | Sasikumar et al. |
| 2023/0167076 | A1 | 6/2023 | Sasikumar et al. |
| 2023/0167077 | A1 | 6/2023 | Yu |
| 2023/0278970 | A1 | 9/2023 | Sasikumar et al. |

FOREIGN PATENT DOCUMENTS

| | | |
|---|---|---|
| CN | 105814028 A | 7/2016 |
| CN | 111163772 A | 5/2020 |
| JP | 2016/532710 A | 10/2016 |
| JP | 2016/539662 A | 12/2016 |
| KR | 20160081897 A | 7/2016 |
| WO | WO-2001/014557 A1 | 3/2001 |
| WO | WO-2002/079499 A1 | 10/2002 |
| WO | WO-2002/086083 A2 | 10/2002 |
| WO | WO-2003/042402 A2 | 5/2003 |
| WO | WO-03/070711 A1 | 8/2003 |

(Continued)

OTHER PUBLICATIONS

Lala, et al. Cancer and Metastasis Reviews (1998), 17(1), 91-106.*
Golub, et al. Science (1999), vol. 286, 531-537.*
Cancer [online], [retrieved on Jun. 30, 2023]. Retrieved from the internet, URL: https://medlineplus.gov/cancer.html.*
Anderson et al., "Lag-3, Tim-3, and TIGIT: Co-inhibitory Receptors with Specialized Functions in Immune Regulation," Immunity, 44(5): 989-1004 (2016).
Ardestani et al., "Cell death features induced in Leishmania major by 1,3,4-thiadiazole derivatives," Exp Parasitol, 132(2): 116-122 (2012).
Berge et al., "Pharmaceutical Salts," Journal of Pharmaceutical Sciences, 66(1):1-19 (1977).
Booher et al., "Combination of IRAK4 Inhibitor CA-4948 with BCL2 Inhibitor Venetoclax Induces Tumor Regression in an ABC-DLBCL Xenograft Model", Blood, 130(1): 1534, (2017).

(Continued)

*Primary Examiner* — Shawquia Jackson
(74) *Attorney, Agent, or Firm* — Foley Hoag LLP; David P. Halstead; Alexander J. Chatterley

(57) ABSTRACT

The invention relates to crystalline forms of a 3-substituted 1,2,4-oxadiazole compound, including an anhydrous crystalline form, methods of their preparation, and related pharmaceutical preparations thereof. The invention also relates to preparations suitable for pharmaceutical, veterinary, and agriculturally-relevant uses.

12 Claims, 15 Drawing Sheets

(56) References Cited

FOREIGN PATENT DOCUMENTS

| WO | WO-2004/004771 A1 | 1/2004 |
|---|---|---|
| WO | WO-2004/056875 A1 | 7/2004 |
| WO | WO-2005/056550 A2 | 6/2005 |
| WO | WO-2006/121168 A1 | 11/2006 |
| WO | WO-2006/133216 A2 | 12/2006 |
| WO | WO-2007/075749 A2 | 7/2007 |
| WO | WO-2008/011557 A2 | 1/2008 |
| WO | WO-2008/039431 A2 | 4/2008 |
| WO | WO-2008/156712 A1 | 12/2008 |
| WO | WO-2009/006555 A2 | 1/2009 |
| WO | WO-2009/059162 A1 | 5/2009 |
| WO | WO-2009/105712 A1 | 8/2009 |
| WO | WO-2010/051447 A1 | 5/2010 |
| WO | WO-2010/077634 A1 | 7/2010 |
| WO | WO-2011/066389 A1 | 6/2011 |
| WO | WO-2011/082400 A2 | 7/2011 |
| WO | WO-2011/137587 A1 | 11/2011 |
| WO | WO-2011/161699 A2 | 12/2011 |
| WO | WO-2012/129564 A2 | 9/2012 |
| WO | WO-2012/168944 A1 | 12/2012 |
| WO | WO-2013/132317 A1 | 9/2013 |
| WO | WO-2013/144704 A1 | 10/2013 |
| WO | WO-2014/055897 A2 | 4/2014 |
| WO | WO-2014/059173 A2 | 4/2014 |
| WO | WO-2014/100079 A1 | 6/2014 |
| WO | WO-2014/110298 A1 | 7/2014 |
| WO | WO-2014/141104 A1 | 9/2014 |
| WO | WO-2014/147586 A1 | 9/2014 |
| WO | WO-2015/033299 A1 | 3/2015 |
| WO | WO-2015/033301 A1 | 3/2015 |
| WO | WO-2016073470 A1 | 5/2016 |
| WO | WO-2016/142833 A1 | 9/2016 |
| WO | WO-2016/142852 A1 | 9/2016 |
| WO | WO-2016/142886 A2 | 9/2016 |
| WO | WO-2017/055860 A1 | 4/2017 |
| WO | WO-2017/079116 A2 | 5/2017 |
| WO | WO-2018/047143 A1 | 3/2018 |
| WO | WO-2018/051254 A1 | 3/2018 |
| WO | WO-2018/073754 A1 | 4/2018 |
| WO | WO-2019/067678 A1 | 4/2019 |
| WO | WO-2019/087087 A1 | 5/2019 |
| WO | WO-2019/087092 A1 | 5/2019 |

OTHER PUBLICATIONS

Borg et al., "1,2,4-Oxadiazole Derivatives of Phenylalnine: Potential Inhibitors of Substance P Endopeptidase," Eur. J. Med. Chem., 28(10):801-810 (1993).
Brittain. "Polymorphism in pharmaceutical solids," edited by H.G Brittain, D.J.W. Grant (chapter 1) p. 1-10 and J.K. Guillory (Chapter 5) p. 183-226 (1999).
Byrn et al., "Pharmaceutical Solids: A Strategic Approach to Regulatory Considerations," Pharmaceutical Research, 12(7):945-954 (1995).
CAS Registry No. 1252104-30-5 (2013).
CAS Registry No. 1356744-17-6 (2012).
CAS Registry No. 146429-76-5 (2013).
CAS Registry No. 1494629-78-5 (2013).
CAS Registry No. 1496514-97-6 (2013).
CAS Registry No. 1496518-51-4 (2013).
CAS Registry No. 1557852-63-7 (2014).
CAS Registry No. 1848907-06-1 (2016).
CAS Registry No. 1848909-97-6 (2016).
CAS Registry No. 1857027-85-0 (2016).
CAS Registry No. 1868314-35-5 (2016).
CAS Registry No. 1868388-36-6 (2016).
CAS Registry No. 1868393-26-3 (2016).
CAS Registry No. 1869758-25-7 (2016).
CAS Registry No. 1870159-31-1 (2016).
CAS Registry No. 1875311-16-2 (2016).
CAS Registry No. 1875758-09-0 (2016).
CAS Registry No. 1878569-90-4 (2016).
CAS Registry No. 876710-85-9 (2006).
Censi et al., "Polymorph Impact on the Bioavailability and Stability of Poorly Soluble Drugs," Molecules, 20(10): 18759-18776 (2015).
Clinical Trial NCT 02812875., "A Study of CA-170 (Oral PD-L1, PD-L2 and VISTA Checkpoint Antagonist) in Patients With Advanced Tumors and Lymphomas," U.S. National Library of Medicine: 7 pages (2016).
Clinical Trial NCT02671955., "A Study of Safety, Pharmacokinetics, Pharmacodynamics of JNJ-61610588 in Participants With Advanced Cancer," U.S. National Library of Medicine: 9 pages (2016).
Database Registry Chemical Abstracts, STN Accession No. 172410-37-6.
Database Registry Chemical Abstracts, STN Accession No. 197083-27-5.
Dempke et al., "Second-and third-generation drugs for immuno-oncology treatment—The more the better?" Eur J Cancer, 74: 55-72 (2017).
Deng et al., "A New VISTA on combination therapy for negative checkpoint regulator blockade" Journal for Immunotherapy of Cancer, 4(86): 1-7 (2016).
Extended European Search Report for EP Application No. 16761169.8 dated Jul. 2, 2019.
Extended European Search Report for EP Application No. 16761184 dated Jun. 26, 2018.
Extended European Search Report for EP Application No. 17862427.6 dated Jun. 5, 2020.
Extended European Search Report for EP Application No. 21209727.3 dated May 18, 2022.
Extended European Search Report for EP Application No. EP/US18/18863750 dated May 31, 2021.
Extended European Search Report for European Application No. 18162983.3 dated Jun. 27, 2018.
Graham, "Clinical Trials of HIV Vaccines," HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM, pp. 1-20-38.
Guo et al., "Design of oxobenzimidazoles and oxindoles as novel androgen receptor antagonists," Bioorg Med Chem Letts 22(7):2572-2578 (2012).
Harvey, "Immunologic and Clinical Effects of Targeting PD-1 in Lung Cancer," Nature, 96: 214-223 (2014).
Hirayama "Handbook for preparation of crystal of organic compound", Maruzen Co., Ltd 17-23, 37-40, 45-51, 57-65 (2008).
International Preliminary Report on Patentability for International Application No. PCT/IB2018/058526 dated May 14, 2020.
International Search Report and Written Opinion for International Application No. PCT/CN2017/104485 dated Jun. 29, 2018.
International Search Report and Written Opinion for International Application No. PCT/IB2014/064279 dated Dec. 12, 2014.
International Search Report and Written Opinion for International Application No. PCT/IB2016/051266 dated Jul. 8, 2016.
International Search Report and Written Opinion for International Application No. PCT/IB2016/051343 dated Jul. 28, 2016.
International Search Report and Written Opinion for International Application No. PCT/IB2017/056462 dated Jan. 10, 2018.
International Search Report Written Opinion for International Application No. PCT/US2018/053052 dated Jan. 29, 2019.
Jin, "Role of PD-1 in Regulating T-Cell Immunity," Current Topics in Microbiology and Immunology, 350: 17-37 (2010).
Lazorchak et al., "Abstract A36: CA-170, an oral small molecule PD-L1 and VISTA immune checkpoint antagonist, promotes T cell immune activation and inhibits tumor growth in pre-clinical models of cancer," Cancer Immunology Research, 5(S3):A36 (2017).
Lee, "A practical guide to pharmaceutical polymorph screening & selection," Asian J Pharm Sci, 9(4): 163-175 (2014).
Liu et al., "Immune-checkpoint proteins VISTA and PD-1 nonredundantly regulate murine T-cell responses," PNAS, 112(21): 6682-6687 (2015).
Luo et al., "Principles of Cancer Therapy: Oncogene and Non-oncogene Addiction," Cell, 136(5): 823-837 (2009).

(56) References Cited

OTHER PUBLICATIONS

Marechal et al., "1,2,4-oxadiazoles identified by virtual screening and their non-covalent inhibition of the human 20S proteasome," Curr Med Chem 20(18):2351-2362 (2013).
Melero, "Evolving Synergistic Combinations of Targeted Immunotherapies To Combat Cancer", Nature Reviews Cancer 15:457-472 (2015).
Moussebois et al., "Synthese de Deux Nouveaux Acides Amines Phenoliques Comportant un Cycle 1,2,4-Oxadiazole," Helv. Chim. ACTA, 60(1):237-242 (1977).
Newman, "Specialized Solid Form Screening Techniques," Org Process Res Dev, 13(3): 457-471 (2012).
Ozcan et al., "Oxadiazole-Isopropylamieds as Potent and Noncovalent Proteasome Inhibitors," J. Med. Chem., 56(10):3783-3805 (2013).
Palazzo et al., "1,2,4-Oxadiazoles—IV. Synthesis and Pharmacological Properties of a Series of Substituted Aminoalkyl- 1,2,4-Oxadiazoles," J. Med. Chem., 351-367 (1961).
Patwardhan et al., "Structure-Activity Relationship Studies and in Vivo Activity of Guanidine-Based Sphingosine Kinase Inhibitors: Discovery of SphK1- and SphK2—Selective Inhibitors," J. Med. Chem., 58(4):1879-1899 (2015).
Pedoeem et al., "Programmed Death-1 Pathway in Cancer and Autoimmunity," Clinical Immunology, 153: 145-152 (2014).
Rabadi et al., ""The role of VISTA in the tumor microenvironment"" Journal of Cancer Metastasis and Treatment, 8(24): 1-14 (2022).
Rietz et al., "Fragment-Based Discovery of Small Molecules Bound to T-Cell Immunoglobulin and Mucin Domain-Containing Molecule 3 (TIM-3)," J Med Chem, 64: 14757-14772 (2021).
Sasikumar et al., "PD-1 derived CA-170 is an oral immune checkpoint inhibitor that exhibits preclinical anti-tumor efficacy," Communications Biology, 4: 12 pages (2021).
Shi et al., "The Role of PD-1 and PD-L1 in T-cell Immune Suppression in Patients with Hematological Malignancies," Journal of Hematology & Oncology, 6(74): 1-6 (2013).
Skrdla et al., "A Simple Quantitative FT-IR Approach for the Study of a Polymorphic Transformation Under Crystallization Slurry Conditions", Journal of Pharmaceutical and Biomedical Analysis, 25(5-6): 731-739 (2001).
Sureshbabu et al., "Synthesis of 1,2,4-oxadiazole-linked Orthogonally Urethane-Protected Dipeptide Mimetics," Tetrahedron Letters, 49(35): 5133-5136 (2008).
Tagliamento et al., "VISTA: A Promising Target for Cancer Immunotherapy?" Immuno Targets and Therapy, 10: 185-200 (2021).
Takada, "API form screening and selection in drug discovery stage", Pharm Stage, 6(10):20-25. (2007).
Waldmann, "Effective Cancer Therapy Through Immunomodulation," T Annu Rev Med, 57: 65-81 (2006).
Wu et al., "VISTA inhibitors in cancer immunotherapy: a short perspective on recent progresses," RSC Med Chem, 12: 1672-1679 (2021).
Alsaab et al., "PD-1 and PD-L1 Checkpoint Signaling Inhibition for CancerImmunotherapy: Mechanism, Combinations, and Clinical Outcome" Frontiers in Pharmacology, vol. 8, No. 561 (2017).
Ansell, "PD-1 Is Expressed on B-Cells in Waldenstrom Macroglobulinemia and Promotes Malignant Cell Viability and Proliferation" Blood, vol. 124, No. 21 (2014).
Baldoni et al: "A New Reversible and Potent P2Y12 Receptor Antagonist (ACT-246475): Tolerability, Pharmacokinetics, and Pharmacodynamics in a First-in-Man Trial", Clinical Drug Investigation, Nov. 1, 2014.
Cedres et al., "Analysis of Expression of Programmed Cell Death 1 Ligand 1 (PD-L1) in Malignant Pleural Mesothelioma (MPM)" Plos One DOI:10.1371 (2015).
Curiel et al., "Blockade of B7-H1 improves myeloid dendritic cell-mediated anitumor immunity" Nature Medicine, vol. 9, No. 5 (2003).
Swaika et al., "Current state of anti-PD-L1 and anti-PD-1 agents in cancer therapy" Molecular Immunology (2015).
U.S. Appl. No. 15/556,800, Granted.
U.S. Appl. No. 16/945,854, Granted.
U.S. Appl. No. 17/962,976, Pending.
U.S. Appl. No. 15/298,539, Granted.
U.S. Appl. No. 15/713,671, Granted.
U.S. Appl. No. 16/192,030, Granted.
U.S. Appl. No. 16/806,872, Granted.
U.S. Appl. No. 17/192,279, Granted.
U.S. Appl. No. 17/981,695, Pending.
U.S. Appl. No. 16/343,681, Pending.
U.S. Appl. No. 16/761,162, Granted.
U.S. Appl. No. 17/962,096, Pending.
U.S. Appl. No. 16/651,830, Granted.
U.S. Appl. No. 17/350,455, Granted.
U.S. Appl. No. 16/755,439, Granted.
U.S. Appl. No. 17/461,512, Pending.
U.S. Appl. No. 18/197,414, Pending.
U.S. Appl. No. 16/761,964, Granted.
U.S. Appl. No. 17/960,586, Pending.

* cited by examiner

CRYSTAL FORMS OF IMMUNOMODULATORS

RELATED APPLICATIONS

This application is a continuation of U.S. Ser. No. 17/350,445, Jun. 17, 2021, which is a continuation of U.S. Ser. No. 16/651,830, now U.S. Pat. No. 11,040,948, filed Mar. 27, 2020, which is the § 371 National Stage of PCT/US2018/053,052, filed Sep. 27, 2018, which claims the benefit of International Application No. PCT/CN2017/104,485, filed on Sep. 29, 2017. The contents of each of these applications are hereby incorporated by reference in their entirety.

BACKGROUND

The immune system in mammals regulates the activation and inactivation of lymphocytes through various mechanisms during and after an immune response. Among these mechanisms, there are mechanisms that specifically modulate the immune response as and when required.

3-substituted 1,2,4-oxadiazole compounds act as immunomodulators. Thus, 3-substituted 1,2,4-oxadiazole compounds can be used in the treatment of cancer, immune disorders, immunodeficiency disorders, inflammatory disorders, infectious diseases, and transplant rejection.

Given the therapeutic benefits associated with 3-substituted 1,2,4-oxadiazole compounds, there is a need for improved compositions of these compounds. Further, there is a need for improved methods for preparing and formulating 3-substituted 1,2,4-oxadiazole compounds.

SUMMARY

One aspect of the invention relates to an anhydrous crystalline compound having the structure of formula (I),

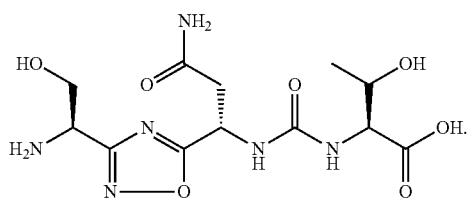

Another aspect of the invention relates to methods for preparing the anhydrous crystalline compounds of formula (I).

In certain embodiments, the present invention provides a pharmaceutical preparation suitable for use in a human patient, comprising an anhydrous crystalline compound of formula (I), and one or more pharmaceutically acceptable excipients. In certain embodiments, the pharmaceutical preparations may be for use in treating or preventing a condition or disease as described herein.

BRIEF DESCRIPTION OF THE DRAWINGS

FIG. 11 shows a comparison of XRPD patterns of anhydrous formula (I) Form A before and after dynamic vapor sorption.

DETAILED DESCRIPTION

Figure 1:
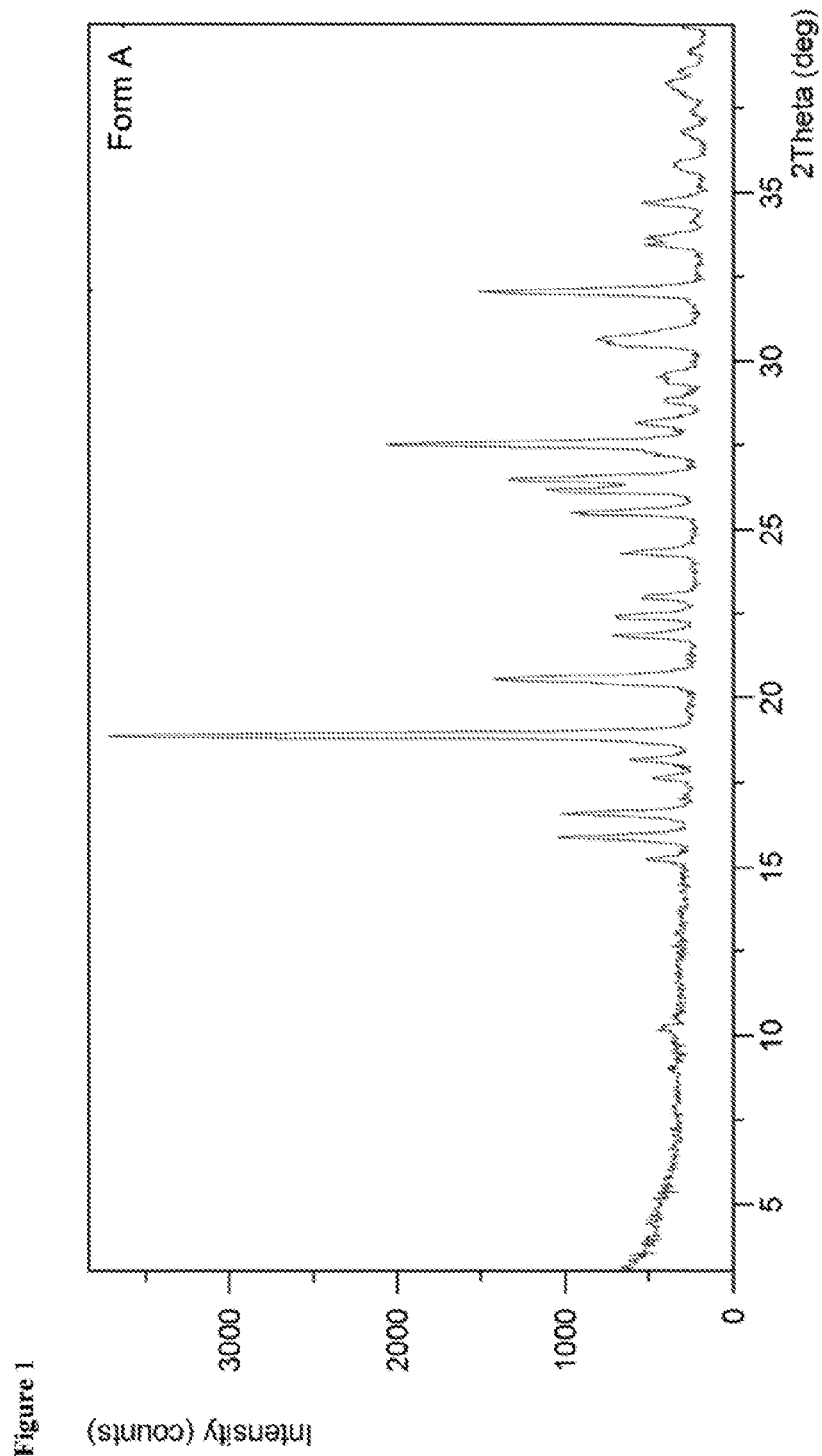
FIG. 1 shows the XRPD patterns of formula (I) Form A.

In certain embodiments, the invention provides an anhydrous crystalline compound having the structure of formula (I),

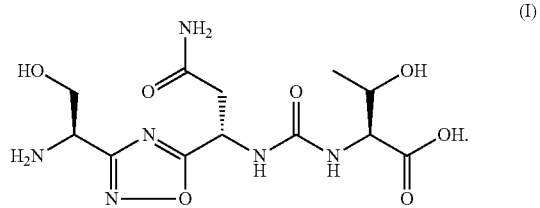 [SMILES: CC(O)[C@H](NC(=O)N[C@@H](CC(N)=O)c1nc([C@@H](N)CO)no1)C(=O)O]

In some embodiments, the invention provides an anhydrous crystalline compound having the structure of formula (I) showing all of the atoms,

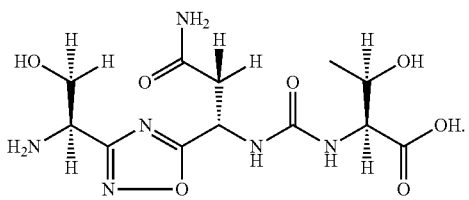
(I)

In certain embodiments, a crystalline compound of formula (I) is not solvated (e.g., the crystal lattice does not comprise molecules of a solvent). In certain embodiments, the crystalline compound of formula (I) is anhydrous, or substantially anhydrous.

Any crystalline compound described herein may be used in the manufacture of a medicament for the treatment of any diseases or conditions disclosed herein.

In certain embodiments, the compounds of the present invention can assemble into more than one crystal formation. These different forms are understood as "polymorphs" herein.

In certain embodiments, the polymorph of the crystalline compound is characterized by powder X-ray diffraction (XRD). θ represents the diffraction angle, measured in degrees. In certain embodiments, the diffractometer used in XRD measures the diffraction angle as two times the diffraction angle θ. Thus, in certain embodiments, the diffraction patterns described herein refer to X-ray intensity measured against angle 2θ.

In certain embodiments, an anhydrous crystalline compound of formula (I) has 2θ values 18.8±0.2, 20.5±02, 26.4±0.2, 27.5±0.2, and 32.0±0.2. In further embodiments, the anhydrous crystalline compound has 2θ values 18.8±0.2, 20.5±0.2, 26.1±0.2, 26.4±0.2, 27.5±0.2, 30.6±0.2, and 32.0±0.2. In yet further embodiments, the anhydrous crystalline compound has 2θ values 15.8±0.2, 16.5±0.2, 18.8±0.2, 20.5±0.2, 25.5±0.2, 26.1±0.2, 26.4±0.2, 27.5±0.2, 30.6±0.2, and 32.0±0.2. In still yet further embodiments, the anhydrous crystalline compound has 2θ values 15.8±0.2, 16.5±0.2, 18.8±0.2, 20.5±0.2, 21.8±0.2, 22.3±0.2, 24.2±0.2, 25.5±0.2, 26.1±0.2, 26.4±0.2, 27.5±0.2, 30.4±0.2, 30.6±0.2, and 32.0±0.2. In some embodiments, the anhydrous crystalline compound has 2θ values selected from the following peaks listed Table 1±0.2.

TABLE 1

Exemplary peaks of Form A

| Pos. [°2Th.] | Height [cts] | FWHM Left [°2Th.] | d-spacing [Å] | Rel. Int. [%] |
| --- | --- | --- | --- | --- |
| 10.151280 | 108.265500 | 0.153504 | 8.71403 | 3.15 |
| 15.169030 | 233.352500 | 0.102336 | 5.84094 | 6.78 |
| 15.811010 | 766.866000 | 0.153504 | 5.60519 | 22.29 |
| 16.494550 | 716.396400 | 0.153504 | 5.37442 | 20.82 |
| 17.600160 | 210.694600 | 0.102336 | 5.03923 | 6.12 |
| 18.132870 | 339.663200 | 0.127920 | 4.89237 | 9.87 |
| 18.820550 | 3441.060000 | 0.153504 | 4.71513 | 100.00 |
| 20.494370 | 1153.954000 | 0.153504 | 4.33366 | 33.53 |
| 21.789780 | 459.031400 | 0.127920 | 4.07886 | 13.34 |
| 22.335970 | 447.623700 | 0.153504 | 3.98034 | 13.01 |
| 22.935230 | 293.402500 | 0.153504 | 3.87768 | 8.53 |
| 24.235630 | 427.814300 | 0.153504 | 3.67248 | 12.43 |
| 25.446040 | 679.351300 | 0.153504 | 3.50047 | 19.74 |
| 26.095330 | 820.166200 | 0.127920 | 3.41483 | 23.83 |
| 26.444450 | 1109.730000 | 0.153504 | 3.37053 | 32.25 |
| 27.454720 | 1759.547000 | 0.153504 | 3.24876 | 51.13 |

TABLE 1-continued

Exemplary peaks of Form A

| Pos. [°2Th.] | Height [cts] | FWHM Left [°2Th.] | d-spacing [Å] | Rel. Int. [%] |
| --- | --- | --- | --- | --- |
| 28.071180 | 323.452300 | 0.179088 | 3.17880 | 9.40 |
| 28.750540 | 189.132400 | 0.179088 | 3.10521 | 5.50 |
| 29.347520 | 184.759400 | 0.204672 | 3.04339 | 5.37 |
| 30.431090 | 460.327500 | 0.127920 | 2.93745 | 13.38 |
| 30.644910 | 576.765100 | 0.127920 | 2.91744 | 16.76 |
| 31.956340 | 1212.746000 | 0.179088 | 2.80065 | 35.24 |
| 33.361460 | 285.081400 | 0.102336 | 2.68583 | 8.28 |
| 33.604180 | 270.969400 | 0.179088 | 2.66699 | 7.87 |
| 34.606870 | 310.585900 | 0.153504 | 2.59198 | 9.03 |
| 35.841170 | 145.972200 | 0.358176 | 2.50550 | 4.24 |
| 36.746890 | 117.362000 | 0.255840 | 2.44579 | 3.41 |
| 37.315610 | 48.631210 | 0.204672 | 2.40982 | 1.41 |
| 38.218310 | 211.915300 | 0.255840 | 2.35495 | 6.16 |
| 38.584910 | 122.935200 | 0.153504 | 2.33341 | 3.57 |
| 39.160630 | 71.010390 | 0.153504 | 2.30043 | 2.06 |

In certain embodiments, an anhydrous crystalline compound of formula (I) has an XRD pattern substantially as shown in FIG. 1, labeled Form A.

In some embodiments, an anhydrous crystalline compound of formula (T) shows a differential scanning calorimetry (DSC) melting/decomposition with an onset temperature in the range selected from about 197° C. to about 210° C., about 201° C. to about 206° C., and about 202° C. to about 205° C. In certain embodiments, a crystalline compound of formula (I) is not solvated (e.g., the crystal lattice does not comprise molecules of a solvent).

In certain embodiments, the invention relates to a pharmaceutical composition comprising an anhydrous crystalline compound of formula (I) and one or more pharmaceutically acceptable excipients. In certain embodiments, the pharmaceutical composition is selected from tablets, capsules, and suspensions.

The term "substantially pure" as used herein, refers to an anhydrous crystalline polymorph that is greater than 90% pure, meaning that it contains less than 10% of any other compound, including the corresponding amorphous compound or an alternative polymorph of the crystalline salt. Preferably, the anhydrous crystalline polymorph is greater than 95% pure, or even greater than 98% pure.

Methods of Making the Anhydrous Crystalline Forms of the Compound of Formula (I)

In certain embodiments, the invention relates to a method for preparing an anhydrous crystalline compound having the structure of formula (I), comprising:
 a) providing a mixture comprising a compound of formula (I) and a solvent; and
 b) crystallizing the compound of formula (I) from the mixture comprising the compound of formula (I).

In certain embodiments, the mixture comprising the compound of formula (I) and the solvent is a reaction mixture.

In certain embodiments, the mixture comprising the compound of formula (I) is a solution. In certain embodiments, the solution comprises a compound of formula (I) dissolved in a solvent. In some embodiments, the solution comprises a crude solid material comprising the compound of formula (I) dissolved in a solvent. In some embodiments, the solution comprises a reaction mixture.

In certain embodiments, the mixture is a slurry or a suspension. In certain embodiments, the slurry or the suspension comprises crude solid material comprising the compound of formula (I).

In certain embodiments of the solutions, slurries, and suspensions disclosed herein, the crude solid material comprising the compound of formula (I) is less than 70% pure, less than 75% pure, less than 80% pure, less than 85% pure, or less than 90% pure with respect to the compound of formula (I). In certain embodiments, the crude solid material comprising the compound of formula (I) is less than 90% pure with respect to the compound of formula (I). In certain embodiments, the crude solid material comprises about 70% to about 90% compound of formula (I). In some embodiments, the purity of the crude solid material is about 70% to about 90% with respect to the compound of formula (I).

In certain embodiments, after crystallization, the compound of formula (I) is substantially pure. In some embodiments, the anhydrous crystalline form of the compound of formula (I) is greater than 90% pure. In some embodiments, the purity of the anhydrous crystalline form of the compound of formula (I) is selected from greater than 90%, greater than 91%, greater than 92%, greater than 93%, greater than 94%, greater than 95%, greater than 96%, greater than 97%, greater than 98%, and greater than 99%. In some embodiments, the purity of the anhydrous crystalline form of the compound of formula (I) is greater than 95%. In some embodiments, the purity of the anhydrous crystalline form of the compound of formula (I) is greater than 98%. In some embodiments, the purity of the anhydrous crystalline form of the compound of formula (I) is selected from about 90%, about 91%, about 92%, about 93%, about 94%, about 95%, about 96%, about 97%, about 98%, and about 99%.

In certain embodiments, the crystalline compound made by the methods of the invention is anhydrous. In certain embodiments, provided herein is a method for preparing an anhydrous crystalline compound having the structure of formula (I):

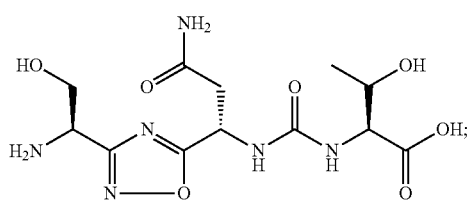

comprising:
a) providing a mixture comprising a compound of formula (I) and a solvent; and
b) crystallizing the compound of formula (I) from the mixture comprising the compound of formula (I).

In some embodiments, solvent vapor slowly diffuses into a solid sample.

In certain embodiments, the mixture comprising the compound of formula (I) is a solution, and the step of crystallizing the compound from the mixture comprises bringing the solution to supersaturation to cause the compound of formula (I) to precipitate out of solution.

In certain embodiments, bringing the mixture comprising the compound of formula (I) to supersaturation comprises the slow addition of an anti-solvent, such as heptanes, hexanes, ethanol, or another polar or non-polar liquid miscible with an aqueous solution, allowing the solution to cool (with or without seeding the solution), reducing the volume of the solution, or any combination thereof. In certain embodiments, the anti-solvent is ethanol. In certain embodiments, bringing the mixture comprising the compound of formula (I) to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, bringing the mixture comprising the compound of formula (I) to supersaturation comprises adding an anti-solvent, maintaining a solution temperature at ambient temperature or higher, and reducing the volume of the solution, e.g., by evaporating solvent from the solution. In some embodiments, the step of bringing the solution to supersaturation comprises maintaining a solution temperature at ambient temperature or higher. In some embodiments, the step of bringing the solution to supersaturation comprises maintaining a solution temperature above about 20° C. In some embodiments, the step of bringing the solution to supersaturation comprises maintaining a solution temperature at about 20° C., about 25° C., about 30° C., about 35° C., about 40° C., about 45° C., about 50° C., about 55° C., about 60° C., about 65° C., or about 70° C.

In certain embodiments, the preparation method further comprises isolating the crystals, e.g., by filtering the crystals, by decanting fluid from the crystals, or by any other suitable separation technique. In further embodiments, the preparation method further comprises washing the crystals.

In certain embodiments, the preparation method further comprises inducing crystallization. The method can also comprise drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.).

In other embodiments, the solvent is acetonitrile, diethyl ether, N,N-dimethylacetamide (DMA), dimethylformamide (DMF), dimethylsulfoxide (DMSO), dichloromethane, ethanol, ethyl acetate, heptanes, hexanes, isopropyl acetate, methanol, methylethyl ketone, N-methyl-2-pyrrolidone (NMP), tetrahydrofuran, toluene, 2-propanol (isopropanol), 1-butanol, water, or any combination thereof. In some embodiments, the solvent is dichloromethane. In some embodiments, the solvent is tetrahydrofuran.

In some embodiments, the anti-solvent is selected from tetrahydrofuran, methanol, isopropanol, diethyl ether, ethanol, 1,4-dioxane, acetonitrile, and acetone. In some embodiments, to an aqueous solution comprising the compound of formula (I) is slowly added an anti-solvent.

In some embodiments, the anti-solvent is selected from tetrahydrofuran, methanol, isopropanol, 1,4-dioxane, acetonitrile, and acetone. In some embodiments, an anti-solvent slowly diffuses into an aqueous solution comprising the compound of formula (I).

In some embodiments, a slurry comprising the compound of formula (I) and a solvent were mixed before isolating the solids. In some embodiments, the isolation of the solids is by filtration or centrifugation.

In some embodiments, the slurry is maintained at ambient temperature or higher. In some embodiments, the slurry is maintained at a temperature above about 20° C. In some embodiments, the slurry is maintained at a temperature of about 20° C., about 25° C., about 30° C., about 35° C., about 40° C., about 45° C., about 50° C., about 55° C., about 60° C., about 65° C., or about 70° C.

In certain embodiments, the solvent is a mixture comprising water. In some preferred embodiments, the solvent is a mixture comprising water and ethanol, isopropanol, methanol, or tetrahydrofuran. In certain preferred embodiments, for example to achieve Form A, the solvent is a mixture comprising water and isopropanol or water and ethanol.

In some embodiments, the solvent is a mixture comprising EtOH:H$_2$O in a volume-to-volume ratio selected from 19:2, 5:1, 2:1, 1:1, and 1:9. In some embodiments, the solvent is a mixture comprising ethanol and water to which additional ethanol or a mixture of ethanol and water is added. In some embodiments, the mixture comprises the compound of formula (I) and a solvent of 2:1 EtOH:H$_2$O (v/v), then a mixture of 19:2 EtOH:H$_2$O is added for crystallization.

In certain embodiments, provided herein is a method for preparing an anhydrous crystalline compound having the structure of formula (I), comprising:
 a) providing a mixture comprising a compound of formula (I) and a solvent;
 b) adding an anti-solvent to the mixture; and
 c) crystallizing the compound of formula (I) from the mixture comprising the compound of formula (I).

In some embodiments of the methods disclosed herein, the method further comprises adding seed crystals.

In some embodiments, crystallization is aided by seeding or seed loading, that is adding seed crystals to the mixture. In some embodiments, the seed crystals are added at a weight percentage of the total mixture selected from about 1 wt %, about 2 wt %, about 3 wt %, about 4 wt %, about 5 wt %, about 6 wt %, about 7 wt %, about 8 wt %, about 9 wt % a, and about 10 wt %. In some embodiments, the seed crystals are added at a weight percentage of the total mixture selected from about 1 wt %, about 2 wt %, about 3 wt %, about 4 wt %, about 5 wt %, and about 6 wt %. In some embodiments, the seed crystals are added at a weight percentage of the total mixture selected from 3 wt %, 4 wt %, and 5 wt %.

In some embodiments, the seed crystals are formula (I) Form A seed crystals.

In some embodiments of the methods disclosed herein, the method further comprises adding additional anti-solvent.

In certain embodiments, provided herein is a method for preparing an anhydrous crystalline compound having the structure of formula (I), comprising:
 a) providing a mixture comprising a compound of formula (I) and a solvent;
 b) adding an anti-solvent to the mixture;
 c) adding seed crystals to the mixture;
 d) adding additional anti-solvent to the mixture; and
 e) crystallizing the compound of formula (I) from the mixture comprising the compound of formula (I).

In certain embodiments, washing the crystals comprises washing with a liquid selected from anti-solvent, acetonitrile, ethanol, heptanes, hexanes, methanol, tetrahydrofuran, toluene, water, or a combination thereof. As used herein, "anti-solvent" means a solvent in which the compound crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene. In certain embodiments, the anti-solvent is methanol.

In certain embodiments, washing the crystals comprises washing the anhydrous crystalline compound of formula (I) with a solvent or a mixture of one or more solvents, which are described above. In certain embodiments, the solvent or mixture of solvents is cooled prior to washing.

In certain embodiments, the methods of making the anhydrous crystalline forms of the compound of formula (I) are used to remove one or more impurities from the compound of formula (I). In certain embodiments, the crystallization methods described herein are used for purifying the compound of formula (I), e.g., as a final purification step in the manufacture of the compound.

In certain embodiments, the compound of formula (I) is purified by crystallization. In some embodiments, purification of the compound of formula (I) does not use high-performance liquid chromatography (HPLC), including preparative HPLC. In some embodiments, purification of the compound of formula (I) by crystallization is scalable. Advantages of purification by crystallization include, but are not limited to, removal of soluble impurities, ease of purification process, applicability to large scale synthesis, acceptable yields, and high product purity.

In some embodiments, anhydrous crystalline formula (I) Form A is stable throughout the whole manufacturing process. In some embodiments, the water content and physical properties of anhydrous crystalline formula (I) Form A do not change with humidity. In some embodiments, anhydrous crystalline formula (I) Form A is not hygroscopic. For example, crystals of anhydrous crystalline formula (I) Form A may retain their crystal structure and not change weight by more than 0.5% when exposed to an environment of 75% humidity at 40° C. for a month.

In some embodiments, anhydrous crystalline formula (I) Form A was the form with greater stability. In some embodiments, the anhydrous crystalline formula (I) Form A was formed in water or in a mixture of ethanol and water. In some embodiments, the temperature was above about 10° C., above about 15° C., above about 20° C., above about 25° C., above about 30° C., above about 35° C., above about 40° C., above about 45° C., above about 50° C., above about 55° C., above about 60° C., above about 65° C., or above about 70° C. In some embodiments, the temperature was about 10° C., about 15° C., about 20° C., about 25° C., about 30° C., about 35° C., about 40° C., about 45° C., about 50° C., about 55° C., about 60° C., about 65° C., or about 70° C. In some embodiments, the temperature was about 10° C., about 15° C., about 20° C., about 25° C., or about 30° C. In some embodiments, the temperature was about 20° C.

In some embodiments, the conversion to anhydrous crystalline formula (I) Form A was complete in about 4 h, in about 8 h, in about 12 h, in about 16 h, in about 20 h, in about 1 day, in about 2 days, in about 3 days, in about 4 days, in about 5 days, in about 6 days, in about 7 days. In some embodiments, the conversion to anhydrous crystalline formula (I) Form A was complete in about 2 h, in about 3 h, in about 4 h, in about 5 h, in about 6 h, in about 7 h, in about 8 h, in about 9 h, in about 10 h, in about 11 h, in about 12 h, in about 13 h, in about 14 h, in about 15 h, in about 16 h, in about 17 h, in about 18 h, in about 19 h, in about 20 h, in about 21 h, in about 22 h, in about 23 h, in about 24 h, in about 25 h, or in about 26 h. For example, at 20° C., the conversion to anhydrous crystalline formula (I) Form A was complete in about one day.

Uses of Anhydrous Crystal Forms of the Compound of Formula (I)

The compound of formula (I) is a 3-substituted 1,2,4-oxadiazole compound having the following structure,

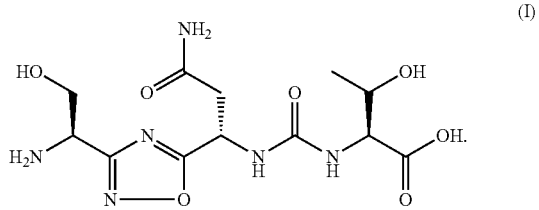 [SMILES: CC(O)[C@H](NC(=O)N[C@@H](CC(N)=O)c1nc([C@@H](N)CO)no1)C(=O)O]

(I)

Functional "exhaustion" (immune dysfunction) among T and B cell subsets is a well-described feature of chronic viral infections, such as hepatitis B and C and HIV viruses. T cell exhaustion was initially described for CD8 T cells in mice chronically infected with lymphocytic choriomeningitis virus clone 13. In the lymphocytic choriomeningitis virus mouse model, repeated antigen stimulation through the T cell antigen receptor drives the sustained expression of T cell inhibitory receptors, including programmed cell death-1 (PD-1) and lymphocyte activation gene-3 (LAG-3), on virus-specific CD8 T cells (J. Illingworth et al., J. Immunol. 2013, 190(3): 1038-1047).

Thus, diseases modulated by an immune response including, but not limited to, cancer, immune disorders, immunodeficiency disorders, inflammatory disorders, infectious diseases, and transplant rejection, can be treated by administering an immunomodulator, such as the compound of formula (I), and compositions disclosed herein. 3-substituted 1,2,4-oxadiazole compounds act as immunomodulators.

In certain embodiments, the compound of formula (I) modulates an immune response in a cell.

In other embodiments, the present disclosure provides a method of modulating an immune response in a cell, comprising contacting the cell with a composition comprising an anhydrous crystalline form of the compound of formula (I), according to any of the above embodiments. In some embodiments, the present disclosure provides a method of modulating an immune response in a cell, comprising contacting the cell with a composition comprising an anhydrous crystalline form of the compound of formula (I), according to any of the above embodiments.

In certain embodiments, the present disclosure provides uses of an anhydrous crystalline form of the compound of formula (I) for the preparation of a medicament, e.g., for the treatment of cancer, immune disorders, immunodeficiency disorders, inflammatory disorders, infectious diseases, and transplant rejection.

In accordance with any of the foregoing embodiments, in certain embodiments, contacting the cell occurs in a subject in need thereof, thereby treating a disease or disorder selected from cancer, immune disorders, immunodeficiency disorders, inflammatory disorders, infectious diseases, and transplant rejection.

In certain embodiments, the present disclosure provides methods for treating cancer, wherein the method comprises administration of a therapeutically effective amount of a composition comprising an anhydrous crystalline form of the compound of formula (I) the subject in need thereof.

In certain embodiments, the present disclosure provides methods for inhibiting growth of tumor cells and/or metastasis by administering a therapeutically effective amount of a composition comprising an anhydrous crystalline form of the compound of formula (I) to the subject in need thereof.

Representative tumor cells include cells of a cancer such as, but not limited to, blastoma (e.g., glioblastoma), breast cancer (e.g., breast carcinoma, primary ductal carcinoma, triple negative breast cancer, estrogen receptor positive (ER+), progesterone receptor positive (PR+), and/or human epidermal growth factor receptor 2 positive (HER2+)), epithelial cancer (e.g., carcinomas), colon cancer, lung cancer (e.g., small cell lung cancer, non-small cell lung cancer (NSCLC), lung adenocarcinoma, and ling squamous cell carcinoma), melanoma (e.g., cutaneous melanoma, ocular melanoma, cutaneous or intraocular malignant melanoma, and lymph node-associated melanoma), prostate cancer (e.g., prostate adenocarcinoma), renal cancer (e.g., renal cell cancer (RCC) and kidney cancer), bone cancer (e.g., osteosarcoma), pancreatic cancer (e.g., pancreatic adenocarcinoma), skin cancer, cancer of the head or neck (e.g., head and neck squamous cell carcinoma), uterine cancer, ovarian cancer (e.g., ovarian carcinoma), colorectal cancer (e.g., microsatellite instability high colorectal cancer and colorectal adenocarcinoma), rectal cancer, cancer of the anal region, cancer of the peritoneum, stomach cancer (e.g., gastric carcinoma and gastrointestinal cancer), testicular cancer, carcinoma of the fallopian tubes, carcinoma of the endometrium, cervical cancer (e.g., carcinoma of the cervix), vaginal cancer (e.g., carcinoma of the vagina), vulval cancer (e.g., carcinoma of the vulva), cancer of the esophagus, cancer of the small intestine, cancer of the endocrine system, thyroid cancer (e.g., cancer of the thyroid gland), cancer of the parathyroid gland, cancer of the adrenal gland, sarcoma (e.g., sarcoma of soft tissue and Kaposi's sarcoma), cancer of the urethra, cancer of the penis, chronic or acute leukemia, (e.g., acute myeloid leukemia, chronic myeloid leukemia, acute lymphoblastic leukemia, chronic lymphocytic leukemia, Hairy cell leukemia, and chronic myeloblastic leukemia), solid tumors of childhood, Hodgkin's lymphoma (HL) (e.g., lymphocyte-rich (LRCHL), nodular sclerosis (NSHL), mixed cellularity (MCHL) and lymphocyte depleted (LDHL)), B-cell lymphomas (e.g., diffuse large B-cell lymphoma (DLBCL)), non-Hodgkin's lymphoma (NHL) (e.g., low grade/follicular non-Hodgkin's lymphoma, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Burkitt's lymphoma, mantle cell lymphoma), AIDS-related lymphoma, cutaneous T-cell lymphoma (e.g., mycosis fundoides) and Waldenstrom's Macroglobulinemia, post-transplant lymphoproliferative disorder (PTLD), lymphocytic lymphoma, primary CNS lymphoma, and T-cell lymphoma), mesothelioma, thymic carcinoma, myeloma (e.g., multiple myeloma), cancer of the bladder (e.g., bladder carcinoma), cancer of the ureter, carcinoma of the renal pelvis, liver cancer (e.g., hepatocellular cancer, hepatic carcinoma, hepatoma), pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, environmentally induced cancers (including those induced by asbestos), and combinations of said cancers.

In other embodiments, for example, the tumor cells may include cells of a cancer selected from prostate cancer, melanoma, breast cancer, colon cancer, prostate cancer, lung cancer, renal cancer, pancreatic cancer, gastric carcinoma, bladder cancer, esophageal cancer, mesothelioma, thyroid cancer, thymic carcinoma, sarcoma, glioblastoma, chronic or acute leukemia, lymphoma, myeloma, Merkel cell carcinoma, epithelial cancer, colorectal cancer, vaginal cancer, cervical cancer, ovarian cancer, and cancer of the head and neck.

In other embodiments, for example, the tumor cells may include cells of a cancer selected from melanoma, triple negative breast cancer, non-small cell lung cancer, renal cell carcinoma, pancreatic cancer, gastric carcinoma, bladder cancer, mesothelioma, Hodgkins's lymphoma, cervical cancer, ovarian cancer, and head and neck squamous cell carcinoma.

In some embodiments, the tumor cells are cells of a cancer selected from small cell lung cancer, multiple myeloma, bladder carcinoma, primary ductal carcinoma, ovarian carcinoma, Hodgkin's lymphoma, gastric carcinoma, acute myeloid leukemia, and pancreatic cancer.

In other embodiments, the tumor cells are cells of a cancer selected from carcinoma of the endometrium, ovarian cancer, Hodgkin's lymphoma, non-Hodgkin's lymphoma, and chronic or acute leukemias including acute myeloid leukemia, chronic myeloid leukemia, acute lymphoblastic leukemia, chronic lymphocytic leukemia, lymphocytic lymphoma, and multiple myeloma.

In some embodiments, the tumor cells are cells of a cancer selected from prostate adenocarcinoma, lung adenocarcinoma, lung squamous cell carcinoma, pancreatic adenocarcinoma, breast cancer and colorectal adenocarcinoma. In certain embodiments, tumor cells are from breast cancer. In some embodiments, the tumor cells are from a breast cancer selected from triple negative breast cancer, estrogen receptor positive (ER+), progesterone receptor positive (PR+), and/or human epidermal growth factor receptor 2 (HER2+). In other embodiments, the tumor cells are from a PAM50+ breast cancer assay panel (Parker, J. S., et al., *J. Clin. Oncol.*, 2009, 27(8): 1160-1167), breast cancer selected from luminal A, luminal B, HER2-enriched, basal-like and normal-like.

In some embodiments, the tumor cells are cells of a cancer selected from triple negative breast cancer, microsatellite instability high colorectal cancer, gastric carcinoma, mesothelioma, pancreatic cancer, and cervical cancer.

In some embodiments, the tumor cells are, and/or the subject is, naïve to immunooncology therapy. Immunooncology uses the subject's immune system to help fight cancer. For example, an immunooncology therapy includes, but is not limited to, atezolizumab (human monoclonal antibody that targets PD-L1), avelumab (human monoclonal antibody that targets PD-L1), brentuximab vedotin (antibody-drug conjugate that targets CD30), durvalamab (human monoclonal antibody that targets PD-L1), ipilimumab (human monoclonal antibody that targets CTLA-4), nivolumab (human monoclonal antibody that targets PD-L1), pembrolizumab (also referred to as lambrolizumab, human monoclonal antibody that targets PD-L1), tremelimumab (human monoclonal antibody that targets CTLA-4), CT-011 (antibody that targets PD-1), MDX-1106 (antibody that targets PD-1), MK-3475 (antibody that targets PD-1), YW243.55.S70 (antibody that targets PD-L1), MPDL3280A (antibody that targets PD-L1), MDX-1105 (antibody that targets PD-L1), and MED14736 (antibody that targets PD-L1). In some embodiments, the immunooncology therapy is selected from an anti-CTLA-4 antibody, an anti-PD-1 antibody, an anti-PD-L1 antibody, an anti-PD-L2 antibody, an anti-TIGIT antibody (e.g., antibodies disclosed in WO 2015/009856).

In other embodiments, the tumor cells are, and/or the subject is responsive to immune checkpoint therapy. In some embodiments, the cancer has shown response to anti-PD1 therapy. For example, the cancer may include non-small cell lung cancer (NSCLC), melanoma, renal cell cancer (RCC), cancer of the bladder, Hodgkin's lymphoma, and head and neck squamous cell carcinoma.

Other embodiments of the present disclosure provide a method of treatment of infection.

Still other embodiments of the present disclosure provide a method of treatment of infection comprising administration of a therapeutically effective amount of a composition comprising an anhydrous crystalline form of the compound of formula (I) to the subject in need thereof.

In certain embodiments, the present disclosure provides uses of an anhydrous crystalline form of the compound of formula (I) for the preparation of a medicament for the treatment of infectious disease, as well as methods of administering a therapeutically effective amount of a composition comprising an anhydrous crystalline form of the compound of formula (I) for the treatment of infectious disease.

In some embodiments, the infectious disease is bacterial infection, viral infection, fungal infection, or parasitic infection, as well as methods of administering a therapeutically effective amount of a composition comprising an anhydrous crystalline form of the compound of formula (I) for the treatment of bacterial infection, viral infection, fungal infection, or parasitic infection.

In some embodiments, for example, bacterial infection may be caused by at least one bacterium selected from anthrax, Bacilli, *Bordetella*, Borrella, botulism, *Brucella, Burkholderia, Campylobacter, Chlamydia,* cholera, *Clostridium, Conococcus, Corynebacterium,* diptheria, *Enterobacter, Enterococcus, Erwinia, Escherichia, Francisella, Haemophilus,* Heliobacter, *Klebsiella, legionella, Leptospira,* leptospirosis, *Listeria,* Lyme's disease, meningococcus, *Mycobacterium, Mycoplasma, Neisseria, Pasteurella, Pelobacter,* plague, Pneumonococcus, *Proteus, Pseudomonas, Rickettsia, Salmonella. Serratia, Shigella, Staphylococcus, Streptococcus, tetanus, Treponema, Vibrio, Yersinia* and *Xanthomonas.*

In other embodiments, for example, viral infection may be caused by at least one virus selected from Adenoviridae, Papillomaviridae, Polyomaviridae, Herpesviridae, Poxviridae, Hepadnaviridae, Parvoviridae, Astroviridae, Caliciviridae, Picornaviridae, Coronaviridae, Flaviviridae, Retroviridae, Togaviridae, Arenaviridae, Bunyaviridae, Filoviridae, Orthomyxoviridae, Paramyxoviridae, Rhabdoviridae, and Reoviridae. In certain embodiments, the virus may be arboviral encephalitis virus, adenovirus, herpes simplex type I, herpes simplex type 2, Varicella-zoster virus, Epstein-barr virus, cytomegalovirus, herpesvirus type 8, papillomavirus, BK virus, coronavirus, echovirus, JC virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, ebola virus, Marburg virus, measles virus, molluscum virus, mumps virus, parainfluenza, respiratory syncytial virus, human metapneumovirus, Hendra virus, Nipah virus, rabies, Hepatitis D, rotavirus, orbivirus, coltivirus, vaccinia virus, and Banna virus.

In other embodiments, for example, fungal infection may be selected from thrush, *Aspergillus (fumigatus, niger*, etc.), *Blastomyces dermatitidis, Candida (albicans, krusei, glabrata, tropicalis*, etc.), *Coccidioides immitis, Cryptococcus (neoformans*, etc.), *Histoplasma capsulatum*, Mucorales (*mucor, absidia*, rhizophus), *Paracoccidioides brasiliensis*, sporotrichosis, *Sporothrix schenkii*, zygomycosis, chromoblastomycosis, lobomycosis, mycetoma, onychonycosis, *piedra pityriasis versicolor*, tinea barbae, tinea capitis, tinea corporis, tinea cruris, tinea tavosa, tinea nigra, tinea pedis, otomycosis, phaeohyphomycosis, and rhinosporidiosis.

In some embodiments, for example, parasitic infection may be caused by at least one parasite selected from *Acanthamoeba, Babesia microti, Balantidium coli*, Entamoeba hystolytica, *Giardia lamblia, Cryptosporidium muris*, Trypanosomatida gambiense, Trypanosoinatida rhodesiense, *Trypanosoma brucei, Trypanosoma cruzi, Leishmania mexicana, Leishimania braziliensis, Leishmania tropica, Leishmania donovani, Toxoplasmna gondmi, Plasmodium vivax, Plasmodium ovale, Plasmodium malariae, Plasmodium falciparum, Pneumocystis carinii, Trichomonas vaginalis, Histomonas meleagridis*, Secementea, *Trichuris trichiura. Ascaris lumbricoides. Enterobius vermicularis, Ancylostoia duodenale*, Naegleria *fowleri, Necator americanus, Nippostrongylus brasiliensis, Strongyloides stercoralis, Wuchereria bancrofti, Dracunculus medinensis*, blood flukes, liver flukes, intestinal flukes, lung flukes, *Schistosoma mansoni, Schistosoma haematobium, Schistosoma japonicum, Fasciola hepalica, Fasciola gigantica, Heterophyes heterophyes*, and Paragonimus *westermani*.

The term "subject" includes mammals (especially humans) and other animals, such as domestic animals (e.g., household pets including cats and dogs) and non-domestic animals (such as wildlife).

As used herein, a therapeutic that "prevents" a disorder or condition refers to a compound that, in a statistical sample, reduces the occurrence or frequency of the disorder or condition in the treated sample relative to an untreated control sample, or delays the onset or reduces the severity of one or more symptoms of the disorder or condition relative to the untreated control sample. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

Pharmaceutical Compositions

In certain embodiments, the present disclosure provides a pharmaceutical composition comprising an anhydrous crystalline form of the compound of formula (I) as disclosed herein, optionally admixed with a pharmaceutically acceptable carrier or diluent.

The present disclosure also provides methods for formulating the disclosed anhydrous crystalline forms of the compound of formula (I) for pharmaceutical administration.

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, an anhydrous crystalline form of the compound of formula (I) of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as an anhydrous crystalline form of the compound of formula (I) of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, an anhydrous crystalline form of the compound of formula (I) of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as an anhydrous crystalline form of the compound of formula (I) of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference in its entirety. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

A suppository also is contemplated as being within the scope of this disclosure.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the anhydrous crystalline form of the compound of formula (I) of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Analytical Methods
X-Ray Powder Diffraction

X-Ray Powder Diffraction (XRPD) patterns were collected on an Empyrean diffractometer or an X'Pert3 diffractometer using CuKα radiation (45 kV, 40 mA) or using a PANalytical Empyrean diffractometer.

The details of the data collection are summarized in Table 2:

TABLE 2

| X-Ray Powder Diffraction Parameters | | | |
|---|---|---|---|
| Instrument Model | Empyrean (Reflection Mode) | PANalytical X' Pert3 (Reflection Mode) | Empyrean (Transmission Mode) |

TABLE 2-continued

X-Ray Powder Diffraction Parameters

| X-Ray wavelength | Cu, kα, Kα1 (Å): 1.540598, Kα2 (Å): 1.544426 Kα2/Kα1 intensity ratio: 0.50 | | |
|---|---|---|---|
| X-Ray tube setting | 45 kV, 40 mA | | |
| Divergence slit | Automatic | Fixed 1/8° | Fixed 1/2° |
| Scan mode | | Continuous | |
| Scan range (°2TH) | | 3°-40° | |
| Scan step time [s] | 17.8 | 46.7 | 33.02 |
| Step size (°2TH) | 0.0167 | 0.0263 | 0.0167 |
| Test Time (s) | 5 min 30 s | 5 min 04 s | 10 min 11 s |

HPLC

Purity analysis was performed on an Agilent HP1100 series system equipped with a diode array detector and using ChemStation software vB.04.03 using the method detailed below in Table 3.

TABLE 3

HPLC Parameters

| Parameter | Value |
|---|---|
| Type of method | Reversed phase with gradient elution |
| Sample Preparation | Diluent, acetonitrile/$H_2O$ = 1:1 |
| Column | ZIC-HILIC, 250 × 4.6 mm, 5 μm |
| Column Temperature | 30° C. |
| Injection Volume | 10 μL |
| Detector Wavelength, Bandwidth | UV at 210 nm |
| Flow Rate | 1.0 mL/min |
| Mobile Phase A | 10 mM $KH_2PO_4$ in $H_2O$ |
| Mobile Phase B | acetonitrile |

| Gradient Timetable | Time (min) | % Mobile Phase A |
|---|---|---|
| | 0.0 | 80 |
| | 2.0 | 80 |
| | 20.0 | 60 |
| | 20.1 | 80 |
| | 30.0 | 80 |

Thermogravimetric Analysis and Differential Scanning Calorimetry

Thermogravimetric analysis (TGA) data were collected using a TA Q500/Q5000 TGA from TA Instruments. Differential scanning calorimetry (DSC) was performed using a TA Q200/Q2000 DSC from TA Instruments. Method parameters are provided in Table 4 below.

TABLE 4

TGA and DSC Parameters

| Parameters | TGA | DSC |
|---|---|---|
| Method | Ramp | Ramp |
| Pan | Platinum, open | Aluminum plate, crimped |
| Temperature | RT-Target Temperature | 25° C.-Target Temperature |
| Ramp rate | 10° C./min | 10° C./min |
| Purge gas | $N_2$ | $N_2$ |

Example 1: Synthesis of Form a by Crystallization from an Isopropanol/Water Mixture Formula (I) (1.00 g) was weighed into a glass vial, and deionised water (10 mL), which afforded a clear solution after being stirred at 35° C. Isopropanol (2 mL) was added followed by formula (I) Form A seed crystals. Charged with 18 mL isopropanol at 35° C. over 8 h, then held for 1 h. Cooled to 25° C. in 2 h, and held at 25° C. for ~1 h. The white solid present was then isolated by filtration, and shown by XRPD analysis to be anhydrous crystalline formula (I) Form A (FIG. 1). The solid was then dried under vacuum at 40° C. for about 20 h (yield not determined).

Example 2: Synthesis of Form a by Crystallization from an Ethanol/Water Mixture A. 5 wt % Seed Crystals, 8 h EtOH Addition Formula (I) (1.02 g) was charged into a 100 mL reactor with deionised water (10 mL). The mixture was stirred (about 300 rpm, about 40 m/min) with an overhead stirrer at 35° C. to afford a clear solution. The solution was charged with 2 mL EtOH followed by 1-2 mg of seed crystals (formula (I) Form A). The seeding point was when the EtOH/$H_2O$ ratio was 1:5 v/v. The My of the seed crystals was 34.2 μm with partly agglomerated crystals, and the D50 of the dry milled seed crystals was 14.9 μm. A cloudy suspension was observed. An additional 50.0 mg of seed crystals (formula (I) Form A) was added, and the mixture was held at 35° C. without stirring for about 10 min. The resulting slurry was stirred at 35° C. for about 8 h while 18 mL of EtOH was slowly added. The mixture was then held at 35° C. without stirring for about 1 h. The mixture was cooled to 20° C. over 1 h and held at temperature without stirring for about 1 h. The white solid present was then isolated by filtration, and washed with 2×10 mL EtOH. The cake was dried at 40° C. under vacuum for 20 h to afford 0.86 g solid (~86% solid yield). The solid was shown by XRPD analysis to be anhydrous crystalline formula (I) Form A (FIG. 1).

B. 5 wt % Seed Crystals, 4 h EtOH Addition

Figure 2:
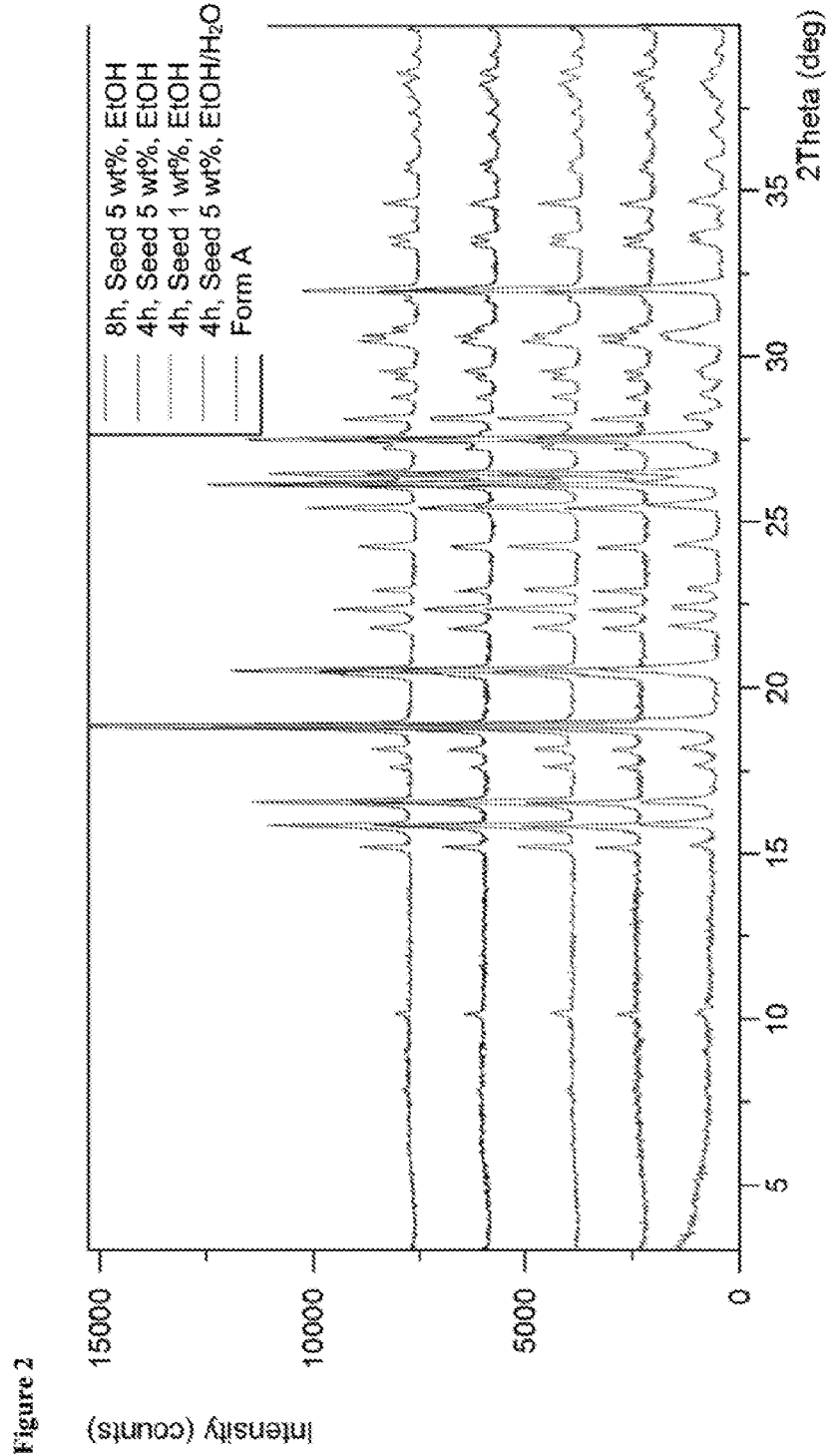
FIG. 2 shows the XRPD patterns of anhydrous formula (I) Form A from different crystallization conditions.

The procedure outlined in Example 2A was followed with 1.00 g of Formula (I) in 10 mL of water, an additional 50.1 mg of seed crystals (formula (I) Form A), and slow addition of 18 mL of EtOH over 4 h to afford 0.85 g solid (~85% solid yield). The solid was shown by XRPD analysis to be anhydrous crystalline formula (I) Form A (FIG. 2).

C. 1 wt % Seed Crystals, 4 h EtOH Addition

The procedure outlined in Example 2A was followed with 1.03 g of Formula (I) in 10 mL of water, an additional 10.6 mg of seed crystals (formula (I) Form A), and slow addition of 18 mL of EtOH over 4 h to afford 0.87 g solid (~87% solid yield). The solid was shown by XRPD analysis to be anhydrous crystalline formula (I) Form A (FIG. 2).

D. 5 wt % Seed Crystals, 4 h EtOH Addition

Formula (I) (1.01 g) was charged into a 100 mL reactor with deionised water (8 mL). The mixture was stirred (about 450 rpm, about 60 m/min) with an overhead stirrer at 35° C. to afford a clear solution. The solution was charged with 1 mL EtOH followed by 1~2 mg of seed crystals (formula (I) Form A). The seeding point was when the EtOH/$H_2O$ ratio was 1:8 v/v. The My of the seed crystals was 34.2 μm with partly agglomerated crystals, and the D50 of the dry milled seed crystals was 14.9 μm. A cloudy suspension was observed. An additional 50.6 mg of seed crystals (formula (I) Form A) was added, and the mixture was held at 35° C. without stirring for about 20 min. The resulting slurry was stirred at 35° C. for about 4 h while 21 mL of EtOH/$H_2O$ (19:1 v/v) was slowly added. The mixture was then held at 35° C. without stirring for about 1 h. The mixture was cooled to 20° C. over 1 h and held at temperature without stirring for about 1 h. The white solid present was then isolated by filtration, and washed with 2×10 mL EtOH. The cake was dried at 40° C. under vacuum for 7 h to afford 0.87 g solid (~87% solid yield). The solid was shown by XRPD analysis to be anhydrous crystalline formula (I) Form A (FIG. 2).

E. Milled Seed Crystals

A 100 mL V style reactor was charged with formula (I) Form A (1.2 g) and held at 10° C. with magnetic stirring using a cross stir bar during the procedure. The reactor was charged with 20 mL of EtOH with a sonication probe. The mixture was sonicated for about 100 min. The white solid present was then isolated by filtration, and washed with 2×10 mL EtOH. The cake was dried at room temperature under vacuum for 10 h.

Agglomerates of rod-like crystals (formula (I) Form A) were obtained in all experiments, with My ranging from 76.2 to 97.6 µm and loose density of 0.13~0.16 g/mL (tap density: 0.19-0.30 g/mL). No significant difference was observed in morphology, particle size distribution (PSD), and loose density among these three experiments (Examples 2A-2C). The morphology and particle size of the products is consistent before and after drying. Not wishing to be bound by any particular theory, agglomerates may be caused by high local supersaturation at the entry point of anti-solvent. Another experiment was performed using EtOH/$H_2O$ (19:2, v/v) as anti-solvent, with an aim to reduce local supersaturation (Example 2D). Agglomeration was mitigated compared with experiments with EtOH as anti-solvent. My of resulting crystals was 63.1 µm and loose density was 0.16 g/mL. Tap density jumped to 0.38 g/mL. Rod-like crystals were observed in the EtOH/water systems using polarized light microscopy of the wet cake and the dried cake (FIGS. 3A-6B). The particle size distribution of anhydrous crystal Form A of formula (I) based on the various crystallization conditions is summarized in Table 5. The particle size is consistent before and after drying with sonication at 30 W for 30 s of the sample. There are differences in the particle size before and after sonication (e.g., 4C dry before v. 4C dry after).

TABLE 5

Particle Size Distribution of Anhydrous Crystal Form A of Formula (I)

| Solvent | Ex. | Mv (µm) | SD | D10 (µm) | D50 (µm) | D90 (µm) | Loose d (g/mL) | Tap d (g/mL) |
|---|---|---|---|---|---|---|---|---|
| EtOH | 4A wet | 76.3 | 39.0 | 26.2 | 68.3 | 132.1 | 0.15 | 0.29 |
| | 4A dry | 76.2 | 39.1 | 25.7 | 68.2 | 131.9 | 0.15 | 0.29 |
| | 4B wet | 80.7 | 39.6 | 29.5 | 74.2 | 136.1 | 0.16 | 0.30 |
| | 4B dry | 81.1 | 40.9 | 27.3 | 73.8 | 138.4 | 0.16 | 0.30 |
| | 4C dry before | 168.7 | 53.0 | 97.4 | 167.4 | 244.5 | | |
| | 4C dry after | 97.6 | 62.2 | 24.1 | 98.2 | 171.4 | 0.13 | 0.26 |
| EtOH/$H_2O$ (19:2, v/v) | 4D dry before | 76.1 | 31.1 | 34.4 | 70.8 | 120.8 | | |
| | 4D dry after | 63.1 | 29.8 | 22.7 | 58.3 | 104.0 | 0.16 | 0.38 |
| Milled Seed | 4E dry before | 145.2 | 164.1 | 6.43 | 56.6 | 391.5 | | |
| | 4E dry after | 34.2 | 19.2 | 3.1 | 14.9 | 69.9 | | |

F. Seed Crystals, EtOH Addition

Formula (I) (1.02 g) was weighed into a glass vial, and deionised water (10 mL) was added, which afforded a clear solution after being stirred at 35° C. EtOH (2 mL) was added, followed by formula (I) Form A seed crystals. Charged 18 mL EtOH at 35° C., then held for 1 h. Cooled to 20° C., held for at 20° C.~1 h. The white solid present was then isolated by filtration, and was shown by XRPD analysis to be formula (I) anhydrous Form A. The solid was then dried under vacuum at RT for about 22 h (0.86 g, ~80% recovery).

G. Seed Crystals, 19:2 EtOH/$H_2O$ Addition

Formula (I) (1.01 g) was weighed into a glass vial, and deionised water (8 mL) was added which afforded a clear solution after being stirred at 35° C. EtOH (1 mL) was added followed by formula (I) Form A seed crystals. Charged the mixture with 21 mL EtOH/$H_2O$ (19:2, v/v), then held for ~1 h. Cooled to 20° C., and held at 20° C. for ~1 h. The white solid present was then isolated by filtration, and was shown by XRPD analysis to be formula (I) anhydrous Form A. The solid was then dried under vacuum at 40° C. for about 7 h (0.87 g, 82% recovery).

H. Seed Crystals, 5:1 EtOH/$H_2O$ Addition

Formula (I) (1.01 g) was weighed into a glass vial, and deionised water (8 mL) was added which afforded a clear solution after being stirred at 35° C. EtOH (1 mL) was added followed by formula (I) Form A seed crystals. Charged the mixture with 30 mL EtOH/$H_2O$ (5:1, v/v), then held for ~1 h. Cooled to 20° C., and held at 20° C. for ~1 h. The white solid present was then isolated by filtration, and was shown by XRPD analysis to be formula (T) anhydrous Form A. The solid was then dried under vacuum at 40° C. for about 6 h (0.84 g, ~80% recovery).

I. 5 wt % Seed Crystals, 8 h EtOH Addition

Formula (I) (1.02 g) was weighed into a 100 mL reactor with the addition of 10 mL deionised water. After being stirred for 10 min to get a clear solution, 2 mL EtOH solvent was added, then 1~2 mg formula (I) Form A seeds were added into the reactor. A muddy or cloudy phenomenon was observed. The solution was kept up stirring for 10 min followed by adding ~50 mg formula (I) Form A seeds. Afterwards the solution was stirred for about 20 min. Then, 18 mL EtOH solvent was added by injection pump over eight hours at 35° C. Then the turbid solution was kept for one hour at 35° C. Lastly, the turbid solution was cooled to 20° C. using one hour, which was then kept at 20° C. for about 11 hours.

Example 3: Synthesis of Form a by Slurry

A. 1:9 EtOH/$H_2O$

Formula (I) (340.8 mg) was weighed into a glass vial. 1 mL of solvent (water/EtOH=9/1, v/v) was added. The resulting slurry was stirred at 50° C. for about 15 h. The wet solid present was then isolated by centrifugation, and was shown by XRPD analysis to be formula (I) anhydrous Form A (yield not determined).

B. 2:1 EtOH/$H_2O$

Formula (I) (29.4 mg) was weighed into a glass vial. 1 mL of solvent (water/EtOH=1/2, v/v) was added. The resulting slurry was stirred at 50° C. for about 15 h. The wet solid present was then isolated by centrifugation, and was shown by XRPD analysis to be formula (I) anhydrous Form A (yield not determined).

C. 1:9 IPA/$H_2O$

Formula (I) (327.3 mg) was weighed into a glass vial. 1 mL of solvent (water/isopropanol=9/1, v/v) was added. The resulting slurry was stirred at 50° C. for about 15 h. The wet solid present was then isolated by centrifugation, and was shown by XRPD analysis to be formula (I) anhydrous Form A (yield not determined).

D. 2:1 IPA/$H_2O$

Formula (I) (29.8 mg) was weighed into a glass vial. 1 mL of solvent (water/isopropanol=1/2, v/v) was added. The resulting slurry was stirred at 50° C. for about 15 h. The white solid present was then isolated by centrifugation, and was shown by XRPD analysis to be formula (I) anhydrous Form A (yield not determined).

Example 4: Thermogravimetric Analysis and Differential Scanning Calorimetry of Formula (I)

Figure 7:
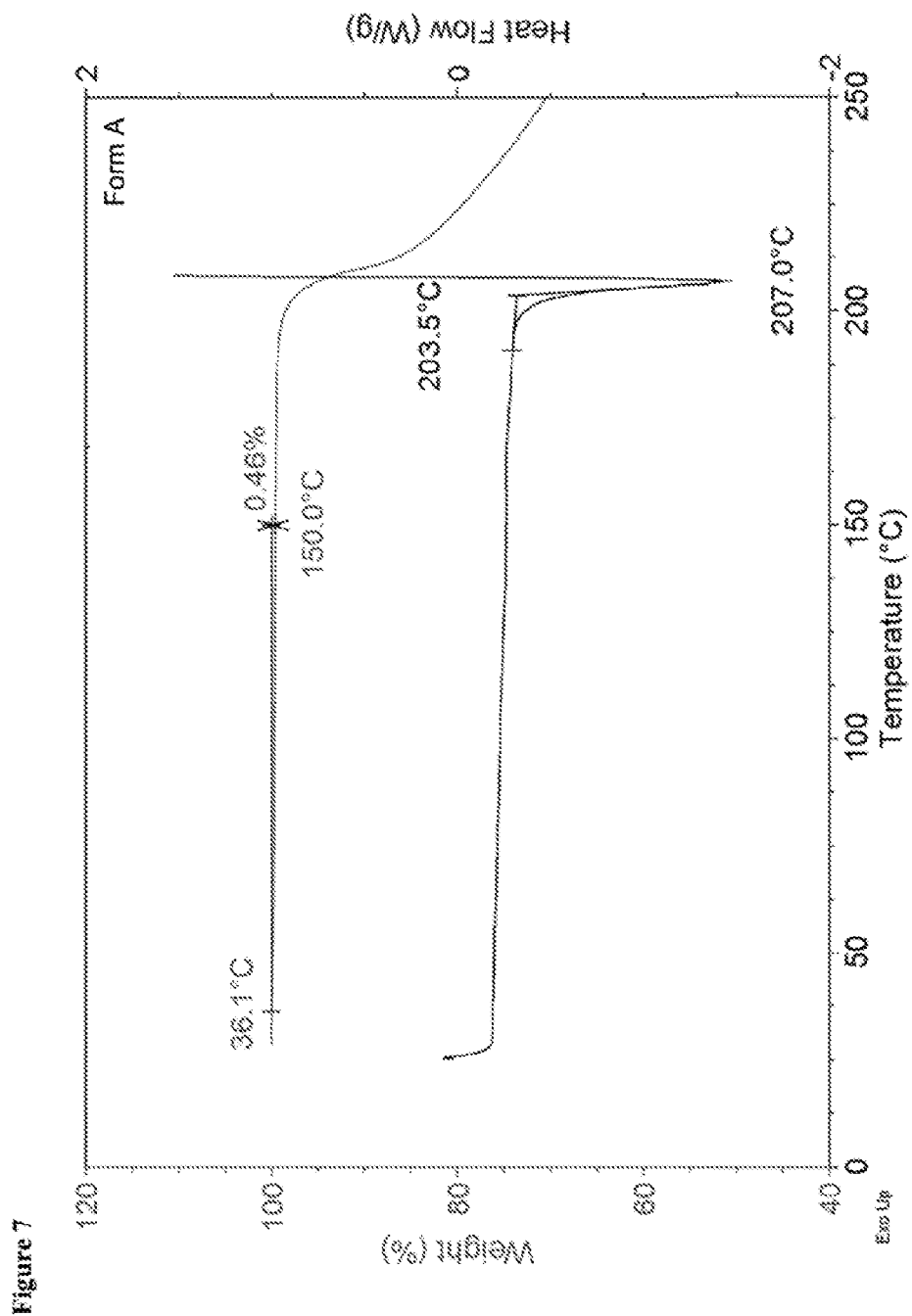
FIG. 7 shows the thermogravimetric analysis and differential scanning calorimetry thermogram of anhydrous Form A.

Thermogravimetric analysis (TGA) of formula (I) anhydrous Form A showed a weight loss of 0.5% up to 150° C., which is consistent with an anhydrate form. Differential scanning calorimetry (DSC) showed an endotherm at 203.5° C. (onset temperature) due to melting/decomposition (FIG. 7).

About 40 mg of a sample of formula (I) Form A was kept at each corresponding condition for one month without significant changes. A shoulder peak was observed in DSC curves of the initial sample and samples after storage at 25° C./60% Relative Humidity (RH) and 40° C./75% RH for one month or for three months. No significant effect of the shoulder peaks on form or HPLC purity was observed. See Table 6.

TABLE 6

Solid Stability of Anhydrous Crystal Form A of Formula (I)

| Condition | Final Form | TGA (%) | DSC (° C., onset) Melting Peak | Shoulder Peak |
|---|---|---|---|---|
| Initial | Form A | 0.40 | 200.6 | 193.7 |
| 25° C., 60% RH, 1 month | Form A | 0.60 | 200.7 | 192.9 |
| 25° C., 60% RH, 3 months | Form A | 2.8 | 201.4 | 194.3 |
| 40° C., 75% RH, 1 month | Form A | 1.0 | 201.1 | 193.4 |
| 40° C., 75% RH, 3 months | Form A | 1.9 | 200.9 | 194.1 |
| 60° C., sealed, 1 month | Form A | 0.6 | 201.0 | No |
| 60° C., sealed, 3 months | Form A | 2.1 | 200.2 | No |
| Seed (after ground), 5° C., sealed | Form A | 0.4 | 199.9 | No |

Example 5: Stability and Forced Degradation Study for Anhydrous Crystalline Formula (I)

Solid Stability

Samples of formula (I) anhydrous crystalline Form A were stored as solids at 25° C./60% RH, 30° C./~56%, and 40° C./75% RH for the time periods listed below. The samples were prepared in duplicate with an offset of 2 weeks. Each replicate was stored in a different container.

Figure 8:
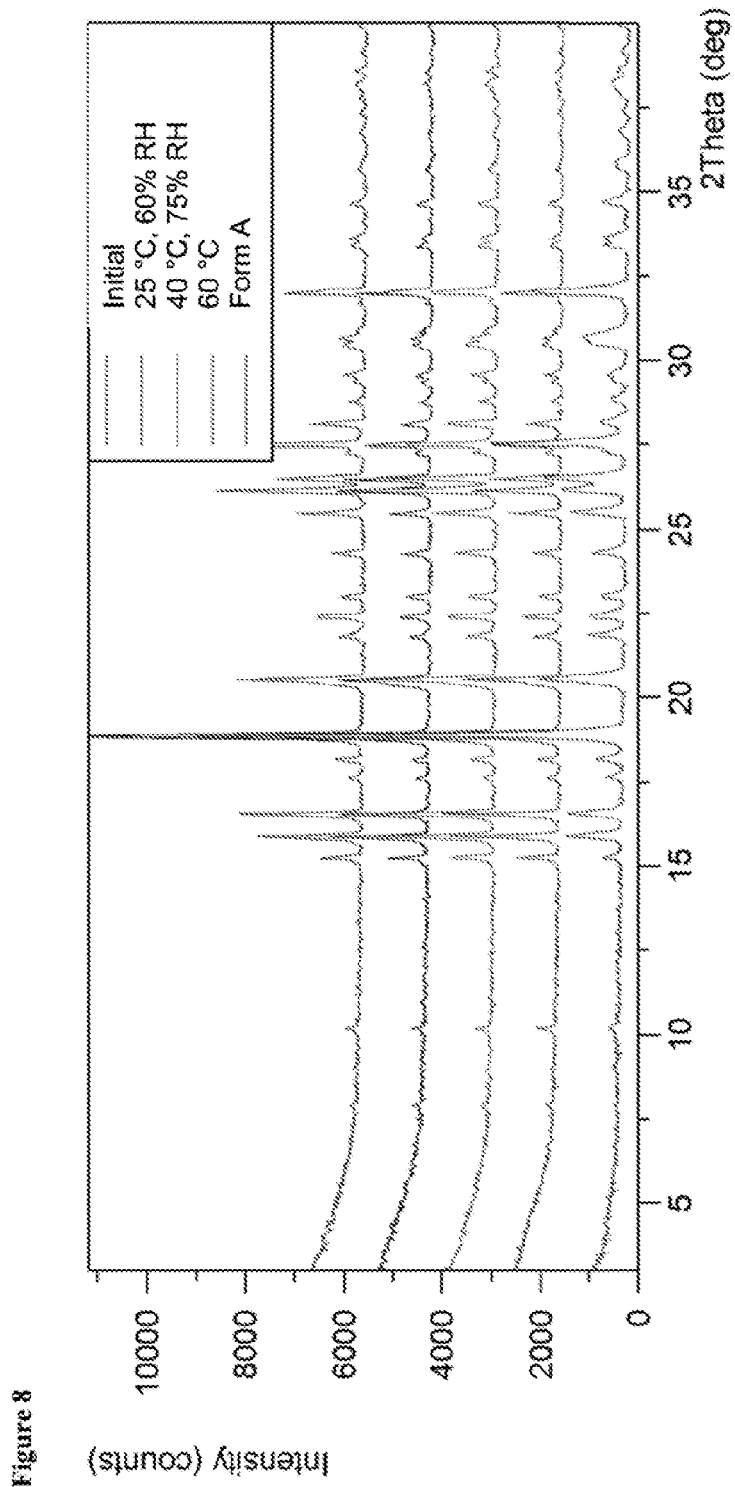
FIG. 8 shows a comparison of XRPD patterns of anhydrous formula (I) Form A initially, at 25° C., 60% relative humidity (RH); 40° C., 75% RH; and 60° C. after three months compared to a Form A reference sample in solid form.

Formula (I) anhydrous crystalline Form A remained unchanged in terms of solid form and particle morphology after storage for one month and three months at 25° C./60% RH, 40° C./75% RH, and 60° C. See FIG. 8 after 3 months. The chemical purity of a solid sample of about 40 mg was also evaluated, and no significant degradation was observed after storage for one month. See Table 7.

TABLE 7

HPLC Purity Profiles of Solid Stability of Anhydrous Crystal Form A of Formula (I)

| Peak | RRT | Initial (area %) | 25° C., 60% RH | 40° C., 75% RH | 60° C., sealed |
|---|---|---|---|---|---|
| | | | 1 month Purity (area %) | | |
| Impurity 1 | 0.63 | 0.63 | <0.05 | <0.05 | <0.05 |
| Impurity 2 | 0.75 | <0.05 | 0.07 | 0.08 | 0.07 |

TABLE 7-continued

HPLC Purity Profiles of Solid Stability of Anhydrous Crystal Form A of Formula (I)

| Peak | RRT | Initial (area %) | 25° C., 60% RH | 40° C., 75% RH | 60° C., sealed |
|---|---|---|---|---|---|
| Impurity 3 | 0.79 | 0.07 | 0.11 | 0.11 | 0.08 |
| Form A | 1.00 | 99.86 | 99.83 | 99.81 | 99.85 |
| | | | 3 months Purity (area %) | | |
| Impurity 1 | 0.63 | 0.63 | <0.05 | <0.05 | <0.05 |
| Impurity 2 | 0.75 | <0.05 | 0.10 | 0.12 | 0.11 |
| Impurity 3 | 0.79 | 0.07 | 0.10 | 0.09 | 0.09 |
| Form A | 1.00 | 99.86 | 99.80 | 99.79 | 99.74 |

Solution Stability

Samples of formula (I) anhydrous crystalline Form A were stored as solutions in water mixed with acetonitrile, tetrahydrofuran, isopropyl alcohol, or ethanol at room temperature and 35° C. for 7-8 days. The sample concentration was about 10 mg/mL and was kept stirring.

At room temperature, a drop in chemical purity was observed from about 99.6% (time 0) to about 99.1% to 99.2% (time 24 h). The main growing impurity observed by HPLC eluted at RRT 0.72 (about 0.36% to about 0.40% at the 24 h time point). (See Table 8.)

TABLE 8

HPLC Purity Profiles of Solution Stability of Formula (I) Anhydrous Crystal Form A at RT

| Solvent | Time (h) | Imp 1 (RRT 0.42) | Imp 2 (RRT 0.53) | Imp 3 (RRT 0.72) | Imp 4 (RRT 0.81) | Imp 5 (RRT 0.82) | Imp 6 (RRT 0.94) | API (RRT 1.00) |
|---|---|---|---|---|---|---|---|---|
| ACN/H$_2$O (1:1, v/v) | 0 | 0.05 | <0.05 | 0.05 | <0.05 | 0.25 | <0.05 | 99.65 |
| | 4 | 0.05 | <0.05 | 0.12 | 0.07 | 0.20 | 0.06 | 99.51 |
| | 24 | 0.05 | 0.05 | 0.36 | <0.05 | 0.20 | 0.10 | 99.24 |
| THF/H$_2$O (1:1, v/v) | 0 | <0.05 | <0.05 | 0.05 | <0.05 | 0.26 | <0.05 | 99.64 |
| | 4 | 0.05 | <0.05 | 0.15 | <0.05 | 0.26 | 0.06 | 99.47 |
| | 24 | 0.05 | <0.05 | 0.38 | <0.05 | 0.23 | 0.10 | 99.19 |
| IPA/H$_2$O (1:2, v/v) | 0 | 0.05 | <0.05 | 0.06 | <0.05 | 0.25 | 0.05 | 99.59 |
| | 4 | <0.05 | <0.05 | 0.15 | 0.06 | 0.22 | 0.06 | 99.52 |
| | 24 | 0.05 | 0.05 | 0.38 | <0.05 | 0.22 | 0.08 | 99.21 |
| EtOH/H$_2$O (1:1, v/v) | 0 | 0.05 | <0.05 | 0.08 | <0.05 | 0.24 | 0.05 | 99.58 |
| | 4 | 0.05 | <0.05 | 0.16 | <0.05 | 0.26 | 0.06 | 99.47 |
| | 24 | 0.05 | 0.08 | 0.40 | <0.05 | 0.22 | 0.14 | 99.11 |

At 35° C., a drop in chemical purity was observed from about 99.6% (time 0) to about 98.200 to 98.400 (time 24 h). The main growing impurity observed by HIPLC eluted at RRT 0.72 (about 1.100% to about 1.3200 at the 24 h time point). (See Table 9.)

TABLE 9

HPLC Purity Profiles of Solution Stability of Formula (I) Anhydrous Crystal Form A at 35° C.

| Solvent | Time (h) | Imp 1 (RRT 0.42) | Imp 2 (RRT 0.53) | Imp 3 (RRT 0.72) | Imp 4 (RRT 0.81) | Imp 5 (RRT 0.82) | Imp 6 (RRT 0.94) | API (RRT 1.00) |
|---|---|---|---|---|---|---|---|---|
| ACN/H$_2$O (1:1, v/v) | 0 | 0.05 | <0.05 | 0.08 | <0.05 | 0.25 | 0.05 | 99.58 |
| | 4 | <0.05 | <0.05 | 0.21 | <0.05 | 0.20 | 0.05 | 99.44 |
| | 24 | 0.09 | <0.05 | 1.10 | 0.06 | 0.17 | 0.15 | 98.42 |
| THF/H$_2$O (1:1, v/v) | 0 | <0.05 | <0.05 | 0.08 | <0.05 | 0.27 | 0.06 | 99.56 |
| | 4 | 0.05 | <0.05 | 0.25 | 0.07 | 0.21 | 0.06 | 99.37 |
| | 24 | 0.08 | <0.05 | 1.24 | 0.05 | 0.17 | 0.16 | 98.30 |
| IPA/H$_2$O (1:2, v/v) | 0 | <0.05 | <0.05 | 0.10 | <0.05 | 0.24 | 0.05 | 99.57 |
| | 4 | 0.05 | <0.05 | 0.25 | 0.07 | 0.20 | 0.08 | 99.35 |
| | 24 | 0.05 | 0.05 | 0.38 | <0.05 | 0.22 | 0.08 | 99.21 |

TABLE 9-continued

HPLC Purity Profiles of Solution Stability of
Formula (I) Anhydrous Crystal Form A at 35° C.

| Solvent | Time (h) | Imp 1 (RRT 0.42) | Imp 2 (RRT 0.53) | Imp 3 (RRT 0.72) | Imp 4 (RRT 0.81) | Imp 5 (RRT 0.82) | Imp 6 (RRT 0.94) | API (RRT 1.00) |
|---|---|---|---|---|---|---|---|---|
| EtOH/H$_2$O (1:1, v/v) | 0 | 0.05 | <0.05 | 0.08 | <0.05 | 0.24 | 0.05 | 99.58 |
| | 4 | 0.05 | <0.05 | 0.16 | <0.05 | 0.26 | 0.06 | 99.47 |
| | 24 | 0.05 | 0.08 | 0.40 | <0.05 | 0.22 | 0.14 | 99.11 |

Example 6: Solubility Measurement for Anhydrous Crystalline Formula (I)

Formula (I) anhydrous Form A showed good solubility in simulated gastric fluid (SGF) of greater than 114.0 mg/mL at room temperature. In a water solution with pH adjustments by NaOH and HCl solutions at room temperature, the solubility of formula (I) Form A was 87.5<S<116.7 at pH 7.08 and 83.5<S<111.3 mg/mL at pH 9.14. The pH values of the aqueous solutions after the solubility test were 5.13 and 5.15, respectively.

Equilibrium solubility of formula (I) anhydrous Form A was measured in the water at 20° C. and 30° C. All samples were equilibrated at temperature for 6 hrs, and the solubility of supernatant was measured by HPLC, while the solids were checked by XRPD. (See Table 10.)

TABLE 10

Equilibrium Solubility of Anhydrous
Crystal Form A of Formula (I)

| Starting Form | Solvent | Temp. (° C.) | Final Form | Solubility (mg/mL) |
|---|---|---|---|---|
| Form A | Water | 20 | Form A | 125.0 |
| Form A | | 30 | Form A | 137.2 |

Figure 9:
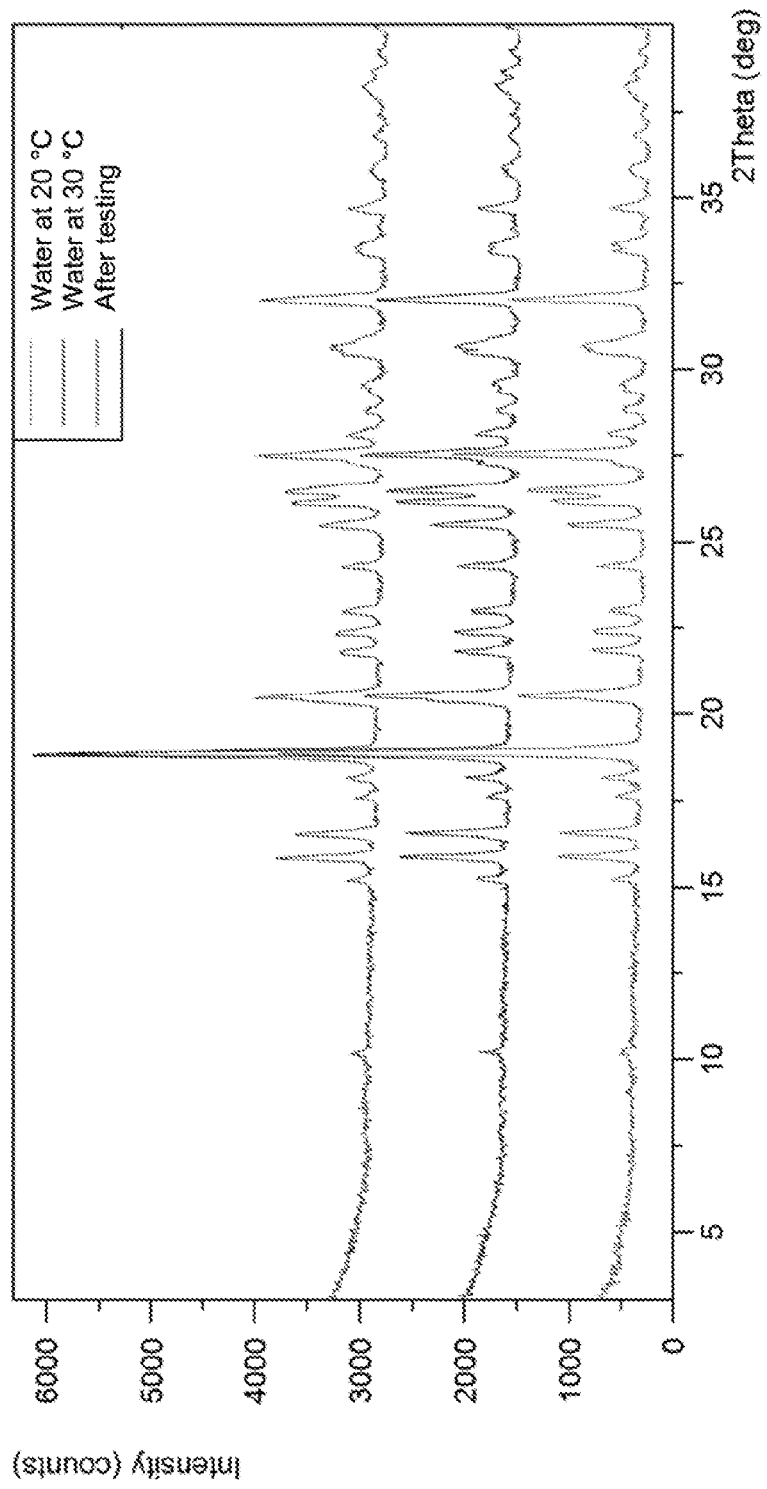
FIG. 9 shows a comparison of XRPD patterns of anhydrous formula (I) Form A in water at 20° C.; in water at 30° C.; and Form A after solubility testing.

No form change was observed during the solubility testing for Form A (FIG. 9).

Example 7: Dynamic Vapor Sorption for Anhydrous Crystalline Formula (I)

Figure 10:
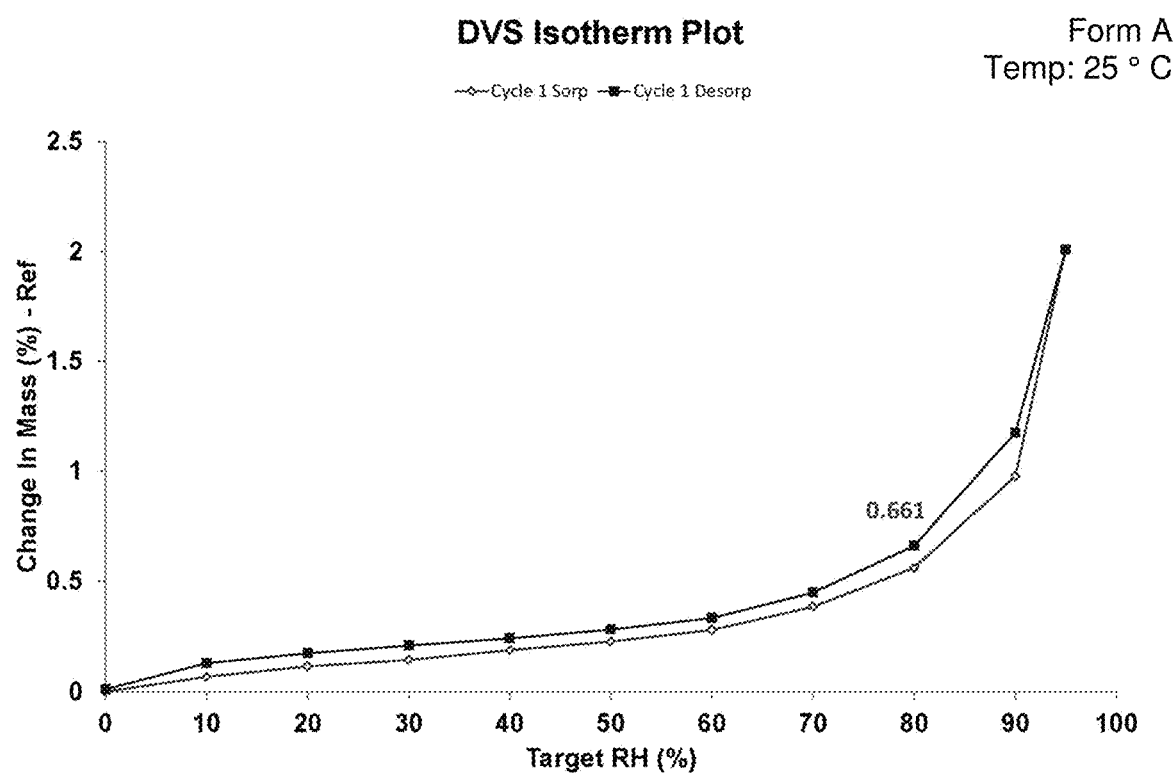
FIG. 10 shows a dynamic vapor sorption isotherm of anhydrous formula (I) Form A.
Figure 1I:
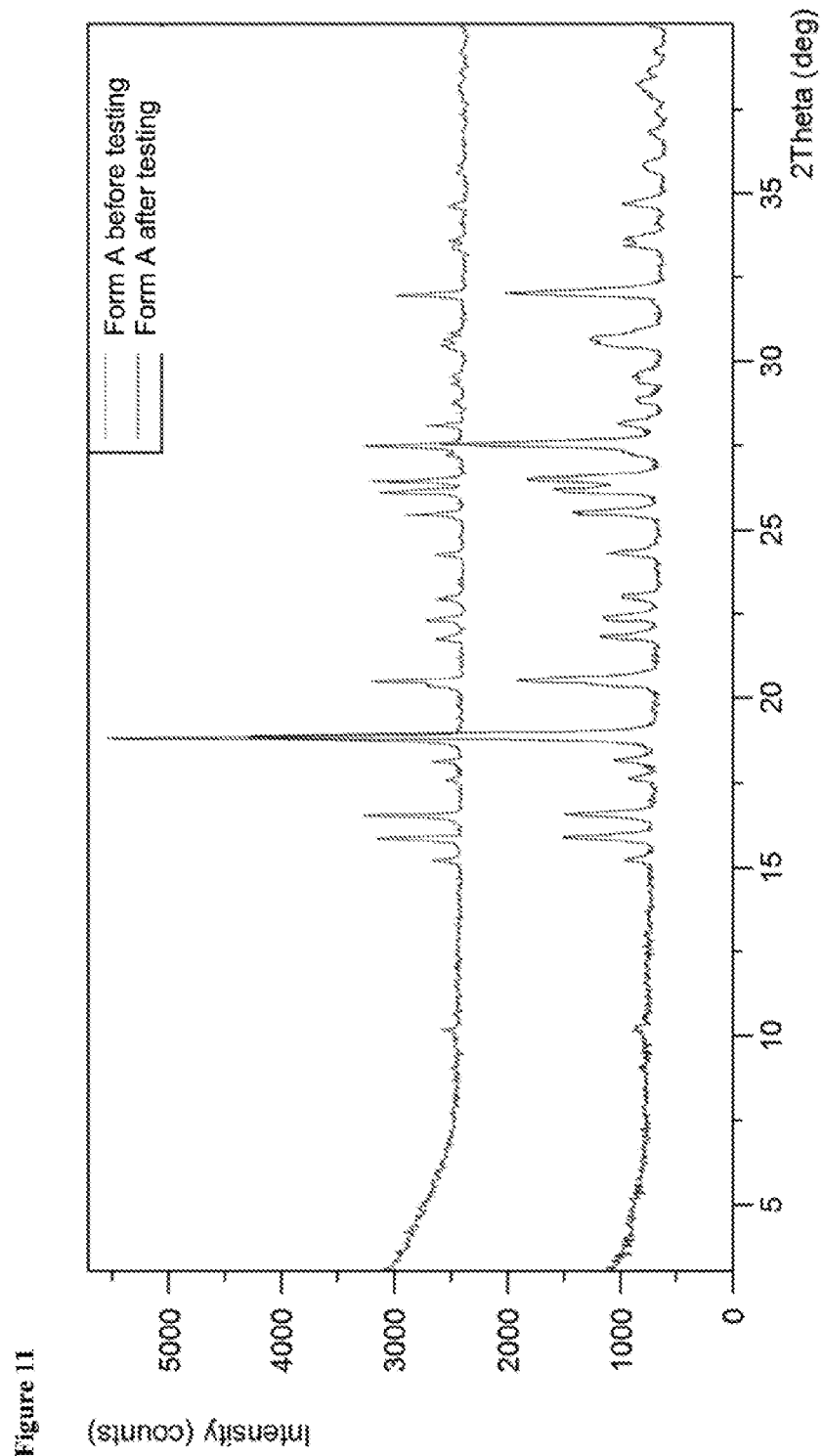

As the dynamic vapor sorption (DVS) results showed, the mass continuously increased with increasing humidity for formula (I) Form A (FIG. 10). Anhydrous Form A also showed about 0.66% mass change up to 80% RH, which indicated that the sample was slightly hygroscopic. No form change was observed during the DVS testing (FIG. 11).

Example 8: Single Crystal Structure Determination

Form A

Figure 3A:
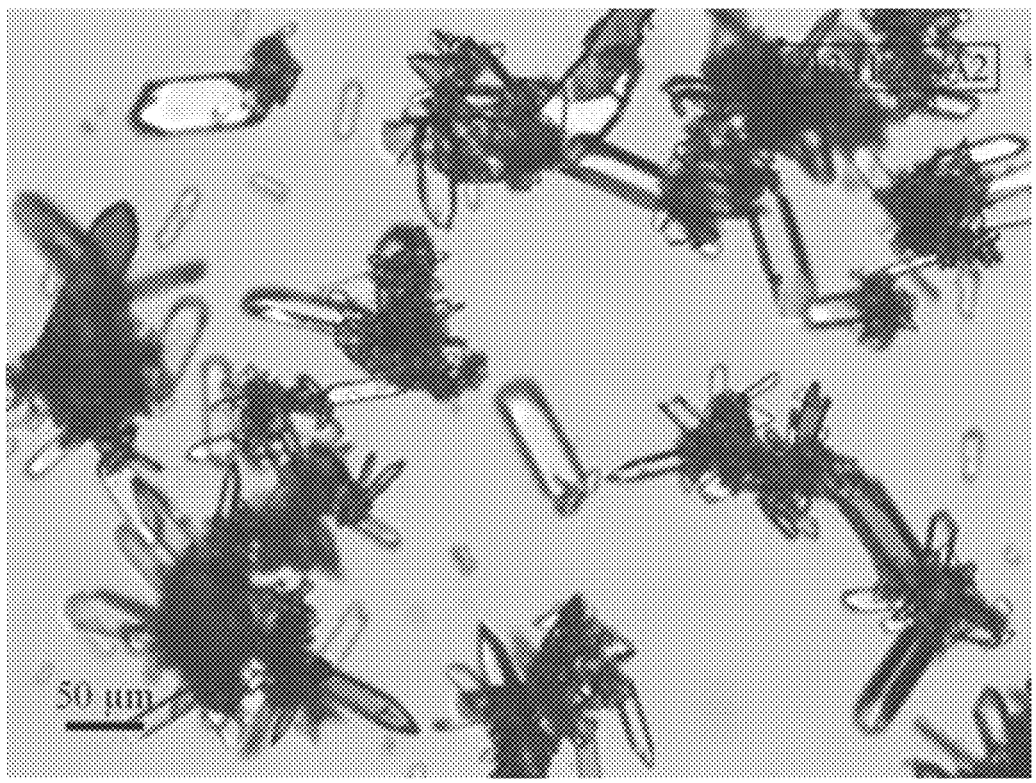
FIG. 3A shows crystals from the wet cake formed with 5 wt % seed crystals and addition of EtOH over 8 h using polarized light microscopy.
Figure 3B:
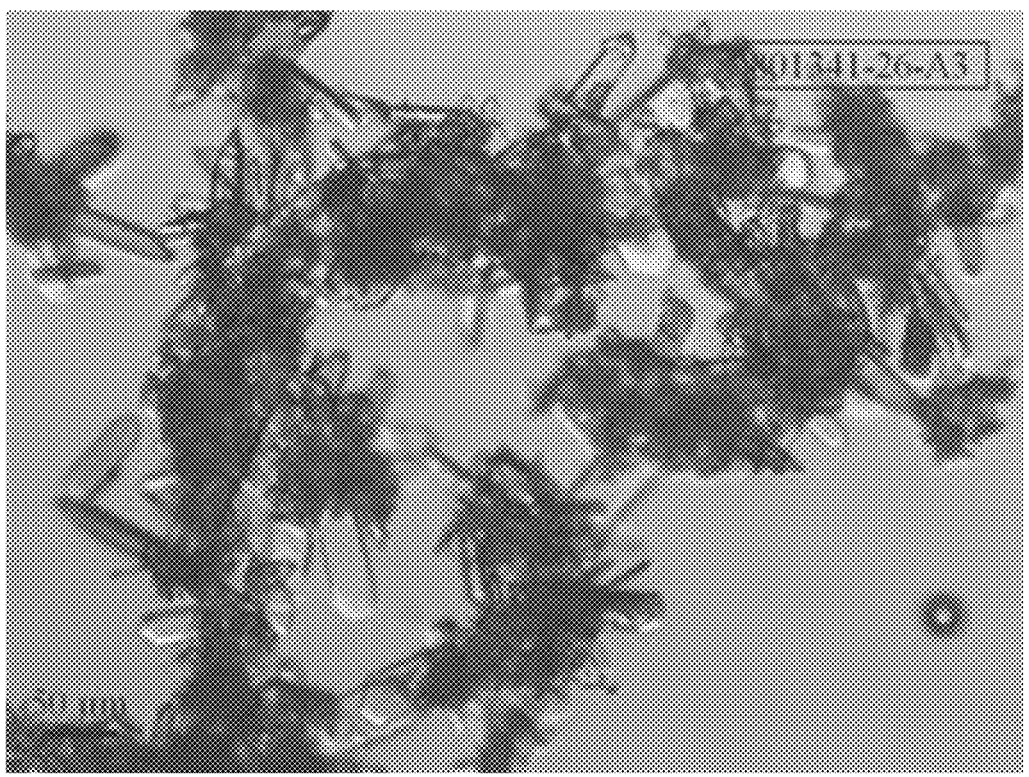
FIG. 3B shows crystals from the dried cake formed with 5 wt % seed crystals and addition of EtOH over 8 h using polarized light microscopy.
Figure 4A:
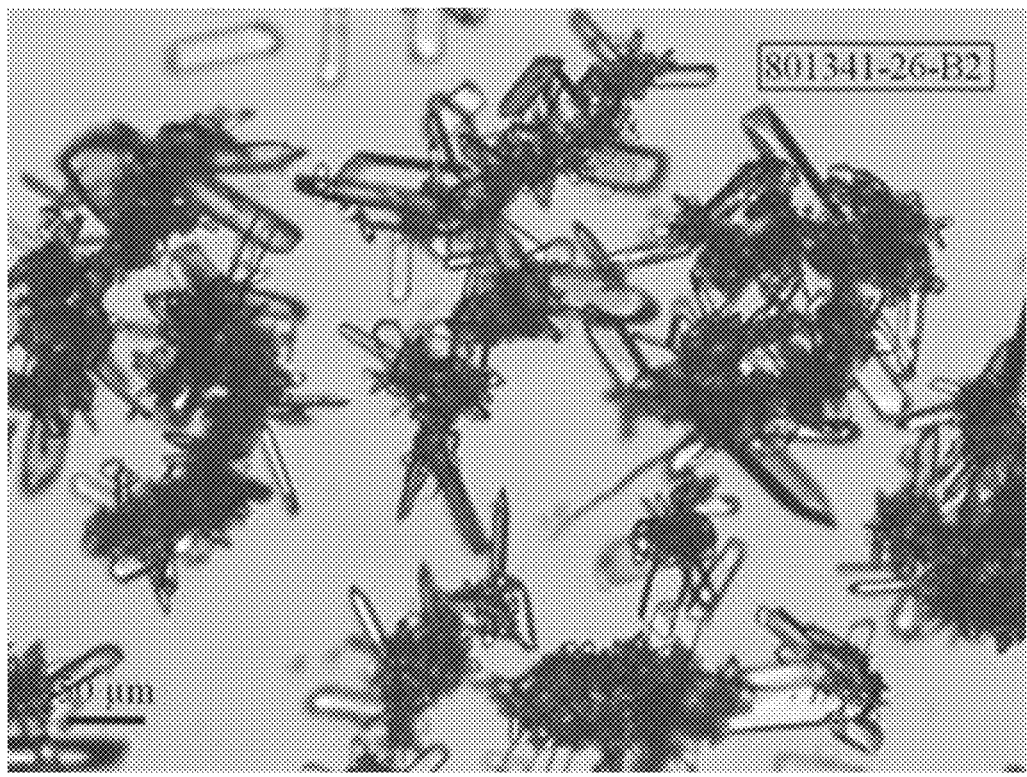
FIG. 4A shows crystals from the wet cake formed with 5 wt % seed crystals and addition of EtOH over 4 h using polarized light microscopy.
Figure 4B:
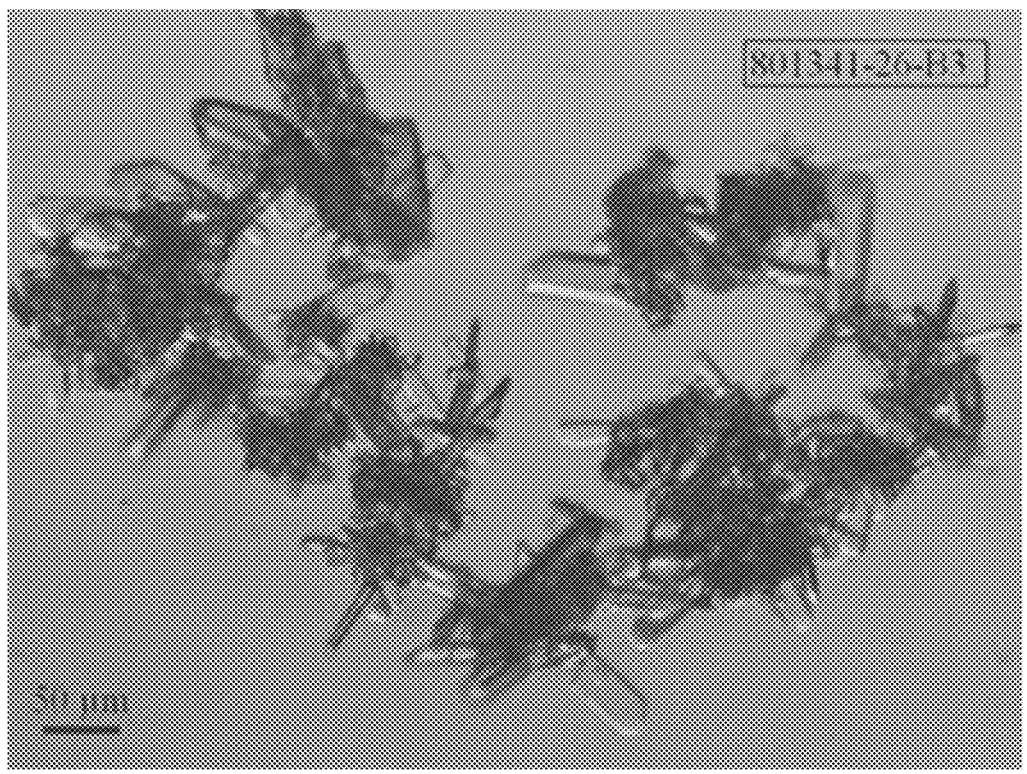
FIG. 4B shows crystals from the dried cake formed with 5 wt % seed crystals and addition of EtOH over 4 h using polarized light microscopy.
Figure 5A:
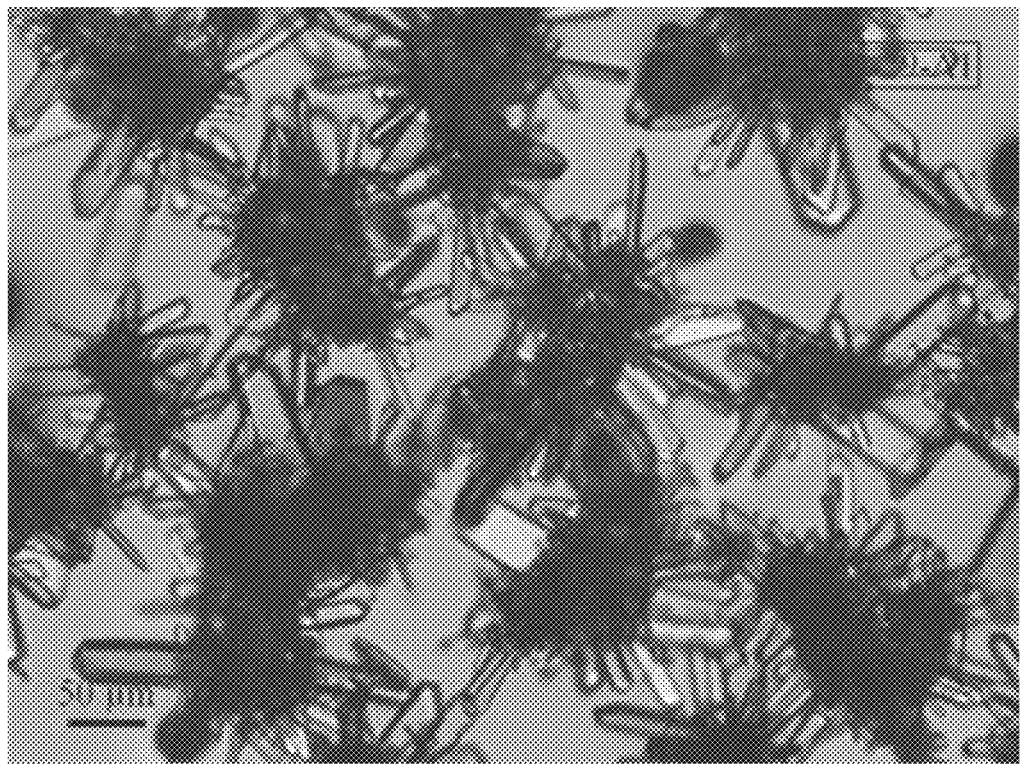
FIG. 5A shows crystals from the wet cake formed with 1 wt % seed crystals and addition of EtOH over 4 h using polarized light microscopy.
Figure 5B:
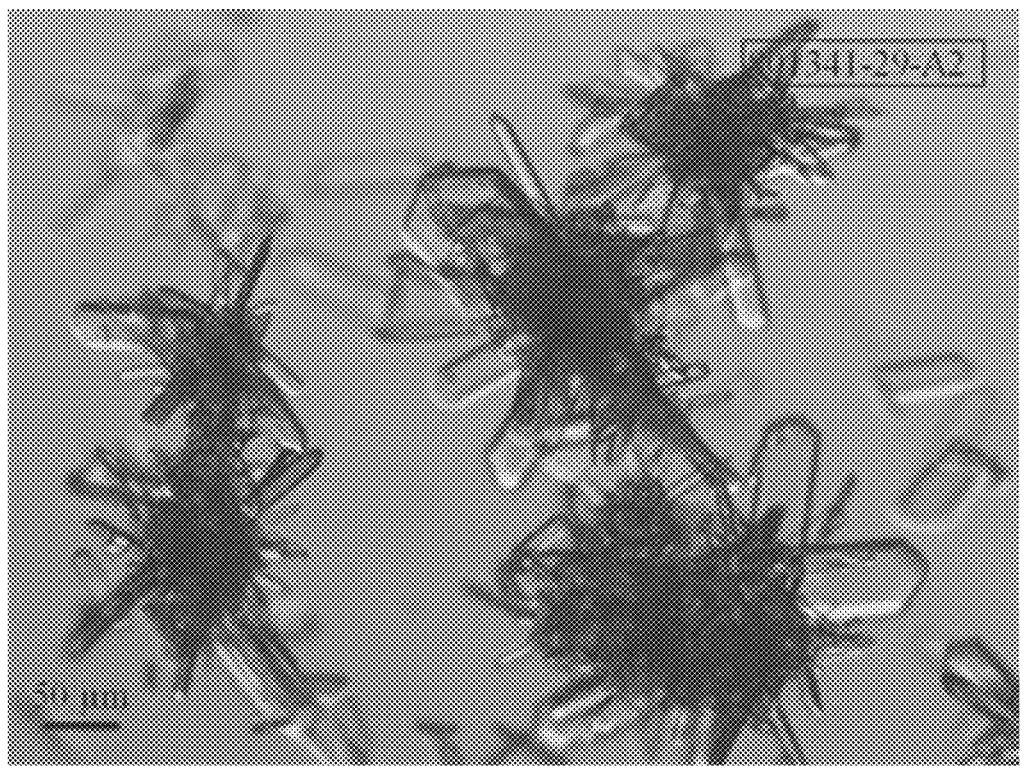
FIG. 5B shows crystals from the dried cake formed with 1 wt % seed crystals and addition of EtOH over 4 h using polarized light microscopy.
Figure 6A:
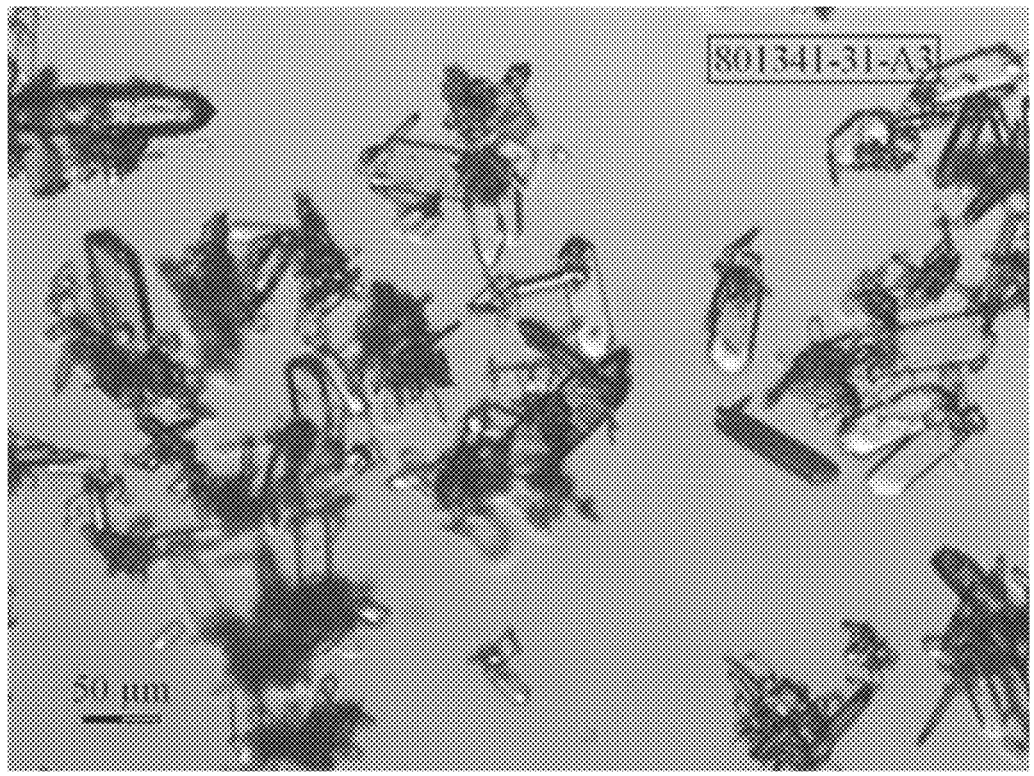
FIG. 6A shows crystals from the wet cake formed with 5 wt % seed crystals and addition of EtOH/H$_2$O over 4 h using polarized light microscopy.
Figure 6B:
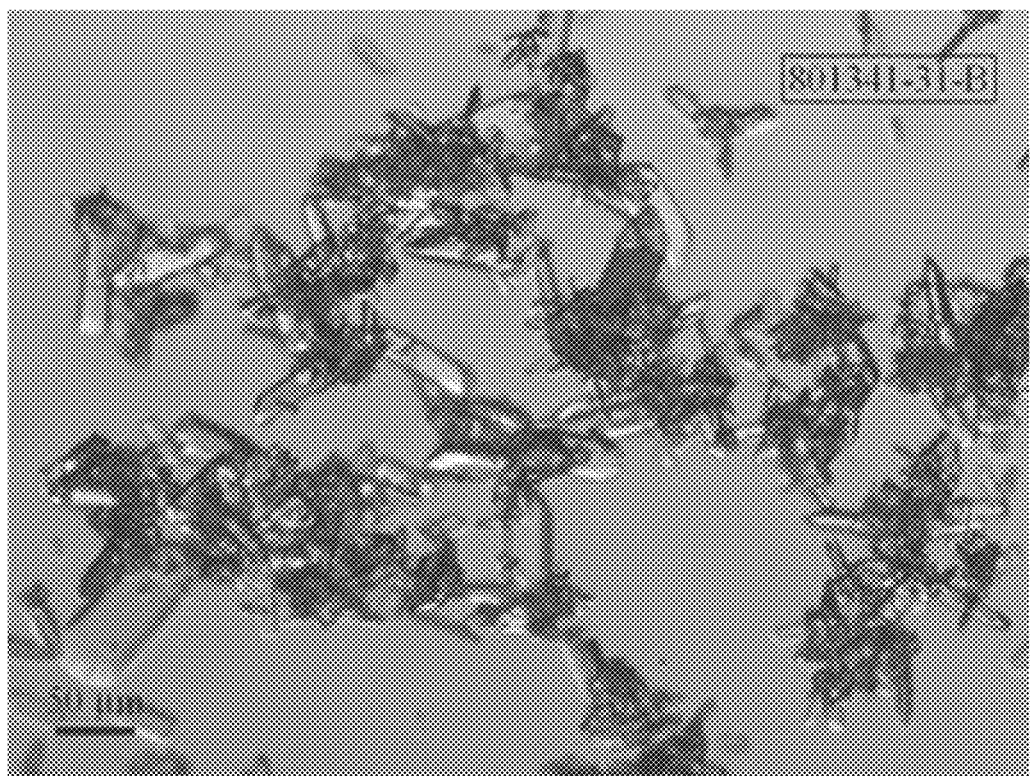
FIG. 6B shows crystals from the dried cake formed with 5 wt % seed crystals and addition of EtOH/H$_2$O over 4 h using polarized light microscopy.

Form A was crystallized from an ethanol/water mixture as described in Example 21. The crystals had a rod-like shape (FIG. 3A). The single crystal X-ray diffraction data was collected at 296 K using Bruker® D8 VENTURE diffractometer (Mo/Kα radiation; λ=0.71073 Å). The structural information and refinement parameters are given in Table 11.

TABLE 11

Structural Information and Refinement Parameters
for Crystal Form A of Formula (I)

| | |
|---|---|
| Empirical formula | C$_{12}$H$_{20}$N$_6$O$_7$ |
| Temperature | 296 K |
| Wavelength | Mo/Kα (λ = 0.71073 Å) |
| Crystal system, space group | Monoclinic, P2$_1$ |
| Unit cell dimensions | a = 10.197(6) Å    α = 90° |
| | b = 6.815(4) Å    β = 106.355(12)° |
| | c = 11.676(5) Å   γ = 90° |
| Volume | 778.6(7) Å$^3$ |
| Z, Calculated density | 2, 1.537 g/cm$^3$ |
| Absorption coefficient | 0.127 mm$^{-1}$ |
| F(000) | 380.0 |
| Crystal size | 0.08 × 0.04 × 0.02 mm$^3$ |
| 2 Theta range for data collection | 6.252 to 55.072° |
| Limiting indices | −13 ≤ h ≤ 8 |
| | −8 ≤ k ≤ 6 |
| | −12 ≤ l ≤ 13 |
| Reflections collected/ Independent reflections | 4208/2897 [R(int) = 0.0424] |
| Completeness | 80.67% |
| Refinement method | Full-matrix least-squares on F$^2$ |
| Data/restraints/parameters | 2897/1/230 |
| Goodness-of-fit on F$^2$ | 1.022 |
| Final R indices [I > 2sigma(I)] | R$_1$ = 0.0568, wR$_2$ = 0.0918 |
| Largest diff. peak and hole | 0.24/−0.28 e · Å$^{-3}$ |
| Flack parameter | −0.1(10) |

Figure 12A:
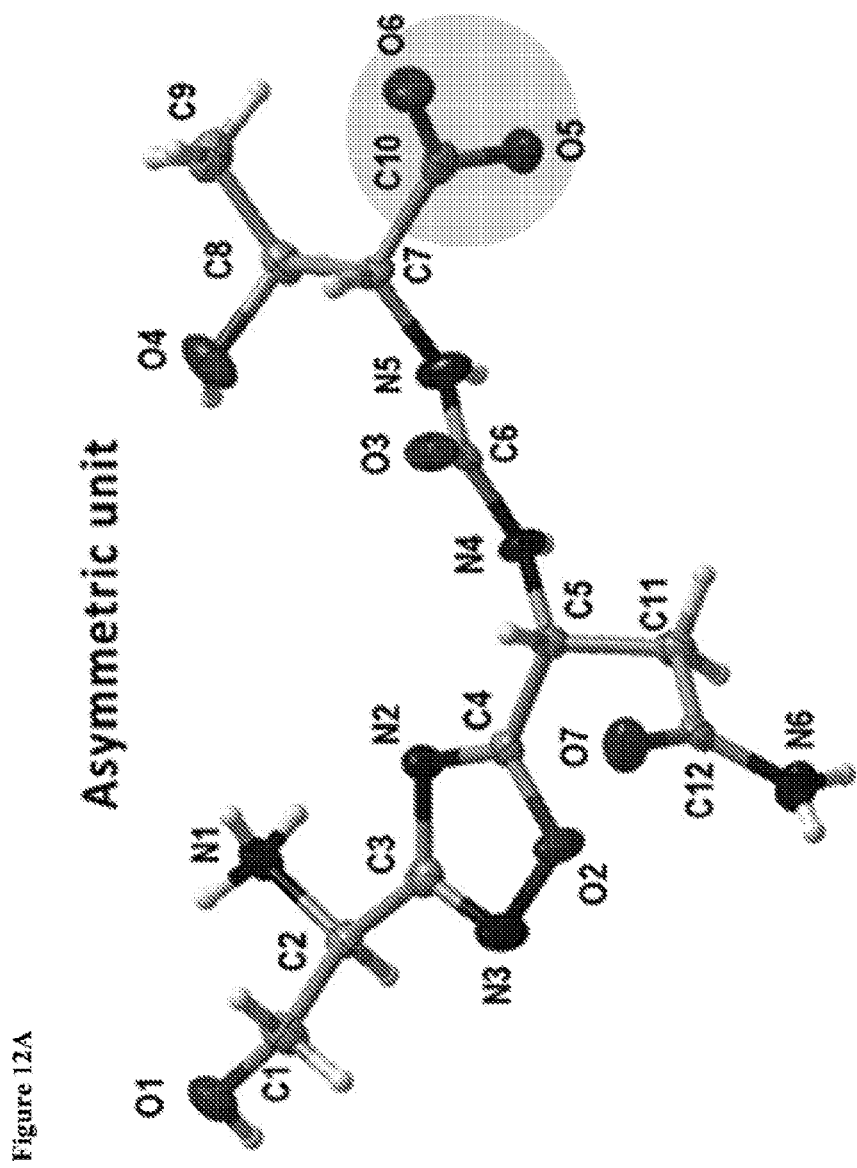
FIG. 12A shows the asymmetric unit of the anhydrous formula (I) Form A single crystal.
Figure 12B:
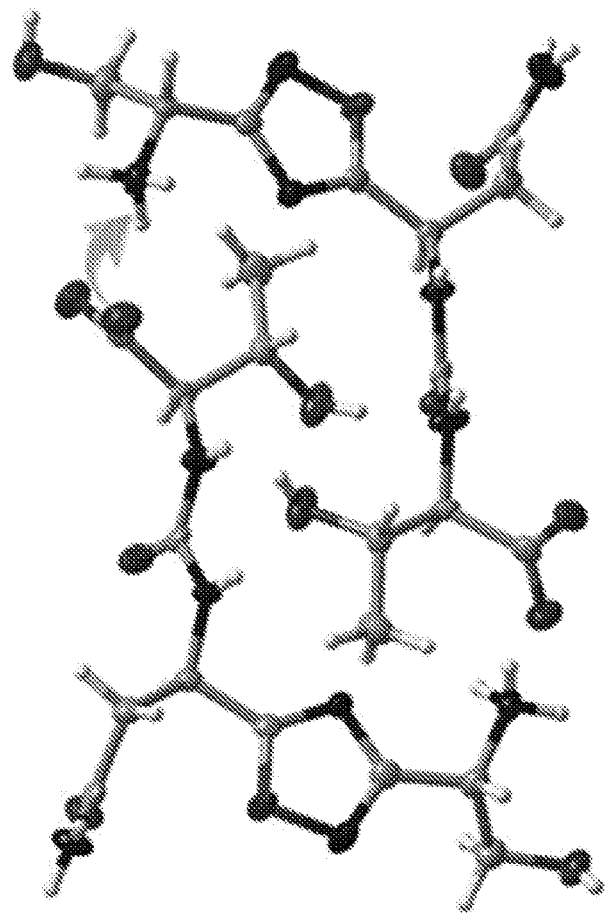
FIG. 12B shows a proposed proton transfer to form a zwitterion in the anhydrous formula (I) Form A crystal.
Figure 12C:
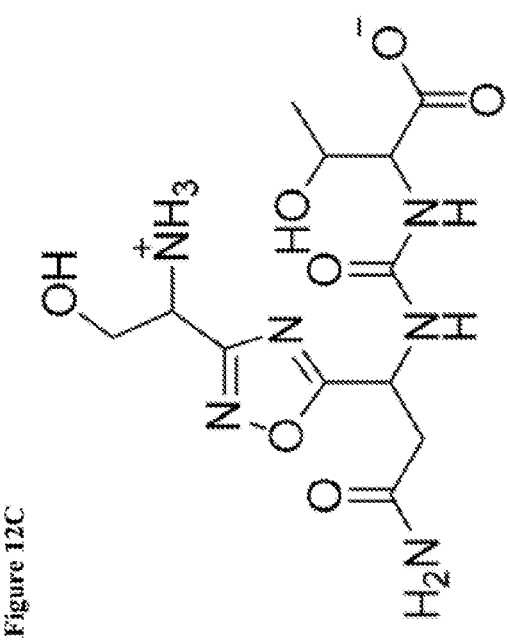
FIG. 12C shows the molecular formula of anhydrous formula (I) Form A in the single crystal.

Single crystal structural analysis confirmed that the crystalline formula (I) Form A is an anhydrate with the asymmetric unit comprised of one formula (I) molecule (FIG. 12A). The bond lengths of the C—O/C═O from the carboxyl group were similar (C—O/C═O: 1.256 Å/1.241 Å). There were three residual electron density peaks (0.35, 0.31, and 0.25 e·Å$^{-3}$) assigned as the hydrogen atoms around the N1 atom at the distances of 1.031 Å, 0.887 Å, and 0.940 Å, respectively. Therefore, it is suggested that the formula (I) molecule was a zwitterion in the anhydrous Form A crystal (FIGS. 12B and 12C). In anhydrous crystalline Form A, adjacent molecules of the compound of formula (I) connect to each other to form the 3-D packing structure via the hydrogen bonds (O—H—O, N—H—O).

Figure 13:
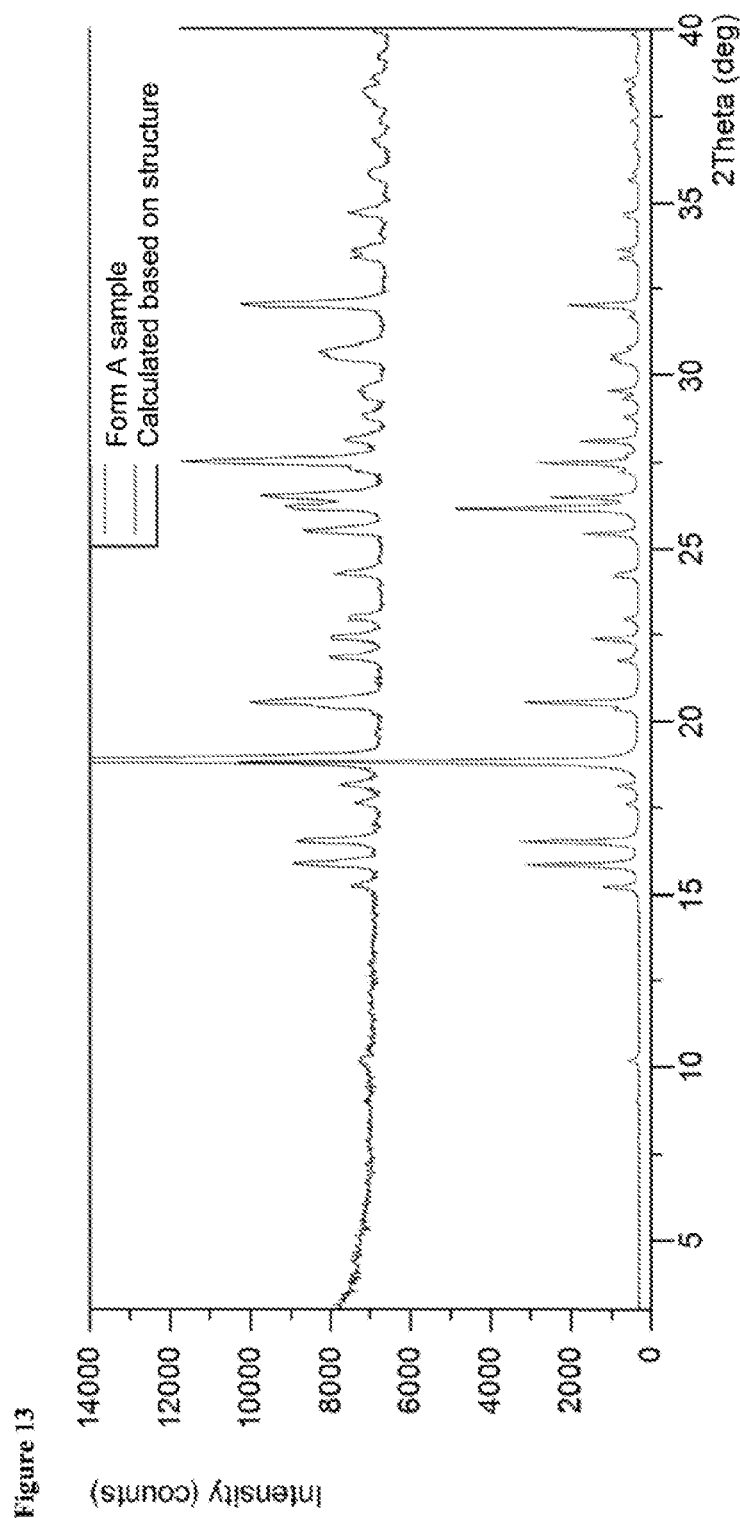
FIG. 13 shows a comparison of XRPD patterns of anhydrous formula (I) Form A based on a sample and as calculated from the single crystal structure.

The absolute configuration of the formula (I) molecule could not be determined with the diffraction data due to the weak anomalous scattering behavior of the formula (I) molecule. The experimental XRPD is compared to the calculated XRPD pattern based on the single crystal structure showing consistent peaks (FIG. 13).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of therapeutically treating cancer in a subject in need thereof comprising administering to the subject an anhydrous crystalline compound having the structure of formula (I),

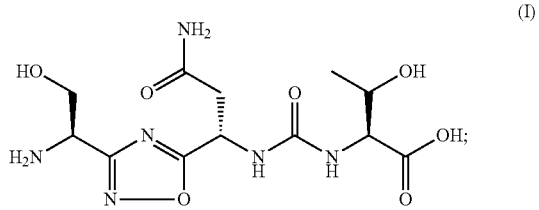 [SMILES: CC(O)[C@H](NC(=O)N[C@@H](CC(N)=O)c1nc([C@@H](N)CO)no1)C(=O)O]

and
wherein the cancer is selected from breast cancer, triple-negative breast cancer, glioblastoma, brain stem glioma, osteosarcoma, bone cancer, primary ductal carcinoma, prostate cancer, colon cancer, cancer of the small intestine, rectal cancer, cancer of the anal region, melanoma, epithelial cancer, skin cancer, renal cancer, kidney cancer, cancer of the head or neck, head and neck squamous cell carcinoma (HNSCC), uterine cancer, ovarian cancer, ovarian carcinoma, colorectal cancer, cancer of the peritoneum, stomach cancer, carcinoma of the fallopian tubes, carcinoma of the endometrium, cancer of the esophagus, leukemia, chronic leukemia, acute leukemia, acute myeloid leukemia, chronic myeloid leukemia, acute lymphoblastic leukemia, chronic lymphocytic leukemia, chronic myeloblastic leukemia, B-cell lymphomas, diffuse large B-cell lymphoma (DLBCL), Hodgkin's lymphoma (HL), non-Hodgkin's lymphoma, small lymphocytic non-Hodgkin's lymphoma, myeloma, multiple myeloma, cancer of the bladder, bladder carcinoma, lung cancer, small cell lung cancer, non-small cell lung cancer (NSCLC), gastric carcinoma, prostate adenocarcinoma, lung adenocarcinoma, lung squamous cell carcinoma, colorectal adenocarcinoma, carcinoma of the renal pelvis, hepatocellular cancer, hepatic carcinoma, liver cancer, mesothelioma, Waldenstrom's macroglobulinemia, nodular sclerosis Hodgkin's lymphoma (NSHL), follicular non-Hodgkin's lymphoma, small lymphocytic non-Hodgkin's lymphoma, T cell lymphoma, cutaneous T-cell lymphoma, small lymphocytic lymphoma, lymphocytic lymphoma, primary CNS lymphoma, pancreatic cancer, and pancreatic adenocarcinoma.

2. The method of claim 1, wherein the anhydrous crystalline compound has 2θ values 18.8±0.2, 20.5±0.2, 26.4±0.2, 27.5±0.2, and 32.0±0.2.

3. The method of claim 1, wherein the anhydrous crystalline compound has 2θ values 18.8±0.2, 20.5±0.2, 26.1±0.2, 26.4±0.2, 27.5±0.2, 30.6±0.2, and 32.0±0.2.

4. The method of claim 1, wherein the anhydrous crystalline compound has 2θ values 15.8±0.2, 16.5±0.2, 18.8±0.2, 20.5±0.2, 25.5±0.2, 26.1±0.2, 26.4±0.2, 27.5±0.2, 30.6±0.2, and 32.0±0.2.

5. The method of claim 1, wherein the anhydrous crystalline compound has 2θ values 15.8±0.2, 16.5±0.2, 18.8±0.2, 20.5±0.2, 21.8±0.2, 22.3±0.2, 24.2±0.2, 25.5±0.2, 26.1±0.2, 26.4±0.2, 27.5±0.2, 30.4±0.2, 30.6±0.2, and 32.0±0.2.

6. The method of claim 1, wherein the anhydrous crystalline compound has 2θ values 10.2±0.2, 15.2±0.2, 15.8±0.2, 16.5±0.2, 17.6±0.2, 18.1±0.2, 18.8±0.2, 20.5±0.2, 21.8±0.2, 22.3±0.2, 22.9±0.2, 24.2±0.2, 25.4±0.2, 26.1±0.2, 26.4±0.2, 27.5±0.2, 28.1±0.2, 28.8±0.2, 29.3±0.2, 30.4±0.2, 30.6±0.2, 32.0±0.2, 33.4±0.2, 33.6±0.2, 34.6±0.2, 35.8±0.2, 36.7±0.2, 37.3±0.2, 38.2±0.2, 38.6±0.2, and 39.2±0.2.

7. The method of claim 1, wherein the cancer is selected from mesothelioma, non-small cell lung cancer (NSCLC), small-cell lung cancer, lung adenocarcinoma, lung squamous cell carcinoma, lung cancer, head and neck squamous cell carcinoma (HNSCC), cancer of the head or neck, Hodgkin's lymphoma, breast cancer, colon cancer, colorectal cancer, ovarian cancer, ovarian carcinoma, triple-negative breast cancer, primary ductal carcinoma, gastric cancer, glioblastoma, renal cancer, kidney cancer, and lymphoma.

8. The method of claim 1, wherein the cancer is selected from small cell lung cancer, multiple myeloma, bladder carcinoma, primary ductal carcinoma, ovarian carcinoma, Hodgkin's lymphoma, gastric carcinoma, acute myeloid leukemia, and pancreatic cancer.

9. The method of claim 1, wherein the cancer is selected from carcinoma of the endometrium, ovarian cancer, Hodgkin's lymphoma, non-Hodgkin's lymphoma, and leukemia.

10. The method of claim 1, wherein the cancer is selected from prostate adenocarcinoma, lung adenocarcinoma, lung squamous cell carcinoma, pancreatic adenocarcinoma, breast cancer, and colorectal adenocarcinoma.

11. The method of claim 1, wherein the cancer is selected from brain stem glioma, osteosarcoma, bone cancer, prostate cancer, cancer of the small intestine, rectal cancer, cancer of the anal region, melanoma, epithelial cancer, skin cancer, uterine cancer, cancer of the peritoneum, stomach cancer, carcinoma of the fallopian tubes, carcinoma of the endometrium, cancer of the esophagus, gastric carcinoma, prostate adenocarcinoma, colorectal adenocarcinoma, carcinoma of the renal pelvis, hepatocellular cancer, hepatic carcinoma, liver cancer, pancreatic cancer, pancreatic adenocarcinoma, myeloma, multiple myeloma, cancer of the bladder, and bladder carcinoma.

12. The method of claim 1, wherein the cancer is selected from leukemia, chronic leukemia, acute leukemia, acute myeloid leukemia, chronic myeloid leukemia, acute lymphoblastic leukemia, chronic lymphocytic leukemia, chronic myeloblastic leukemia, B-cell lymphomas, diffuse large B-cell lymphoma (DLBCL), non-Hodgkin's lymphoma, small lymphocytic non-Hodgkin's lymphoma, Waldenstrom's macroglobulinemia, nodular sclerosis Hodgkin's lymphoma (NSHL), follicular non-Hodgkin's lymphoma, small lymphocytic non-Hodgkin's lymphoma, T cell lymphoma, cutaneous T-cell lymphoma, small lymphocytic lymphoma, lymphocytic lymphoma, and primary CNS lymphoma.

* * * * *